United States Patent [19]
Koenig

[11] Patent Number: 5,730,235
[45] Date of Patent: Mar. 24, 1998

[54] METHOD AND APPARATUS FOR REMOVING MATERIAL FROM A HOLE IN A STRATA FOR USE IN FORCING A MEMBER INTO MATERIAL COMPRISING OR UNDERLYING THIS STRATA

[76] Inventor: Arthur S. Koenig, c/o MDI Labs, Inc. 10863 Hillpoint, San Antonio, Tex. 78217

[21] Appl. No.: 478,202

[22] Filed: Jun. 7, 1995

Related U.S. Application Data

[63] Continuation-in-part of Ser. No. 393,507, Feb. 23, 1995, which is a continuation of Ser. No. 304,804, Sep. 12, 1994, abandoned, which is a continuation of Ser. No. 815,064, Dec. 27, 1991, abandoned, which is a continuation-in-part of Ser. No. 581,181, Sep. 10, 1990, Pat. No. 5,076,392, which is a continuation of Ser. No. 250,321, Sep. 28, 1988, abandoned.

[51] Int. Cl.$^6$ ..................................................... E21B 10/32
[52] U.S. Cl. ............................... 175/230; 82/1.2; 175/20
[58] Field of Search ...................... 175/230, 118, 175/263, 202, 94, 97–99; 82/1.2, 1.4; 408/198, 202, 206, 80, 82, 83, 186, 241 S; 299/41.1; 405/232, 237, 245; 409/218, 190

[56] References Cited

U.S. PATENT DOCUMENTS

| | | | |
|---|---|---|---|
| 2,945,404 | 7/1960 | Baumstark, Jr. et al. | 82/1.2 |
| 3,138,214 | 6/1964 | Bridwell | 175/230 |
| 3,180,436 | 4/1965 | Kellner et al. | 175/94 X |
| 3,225,843 | 12/1965 | Ortloff et al. | 175/230 X |
| 3,827,512 | 8/1974 | Edmond | 175/230 X |
| 4,462,286 | 7/1984 | Erhard | 82/1.4 |
| 4,576,070 | 3/1986 | Fitzgerald | 82/1.2 |
| 4,647,260 | 3/1987 | O'Hara et al. | 408/202 X |
| 4,874,046 | 10/1989 | Hurd | 299/41 X |
| 5,180,209 | 1/1993 | Bieri | 82/1.2 X |

Primary Examiner—William P. Neuder
Attorney, Agent, or Firm—Mark R. Wisner

[57] ABSTRACT

An apparatus for forcing a member or device, such as a sample tube or seismic or geological instrument, through a material such as soil along a selected line of action. The apparatus includes a derrick with first and second plates mounted thereto, the second plate having a locking dog extending through a hole therein for engaging the material, and the first plate being provided with a hydraulic cylinder or other device for forcing the member through the material. The first plate is also provided with an extruder head for releasably mounting the sample-containing sample tube thereto, and the hydraulic cylinder is provided with a plunger releasably mounted to the ram thereof for extruding the sample from the sample tube. The locking dog positively engages the material to provide an apparatus for transmitting the reactive forces resulting from forcing the member through the material to the material. The outer surface of the locking dog is shaped to approximate the shape of the hole and the locking dog is provided with a radially extensible member for engaging a discontinuity or groove in the wall of the hole to transmit the reactive force exerted by the force exerting apparatus to the material. Also provided is an apparatus for removing material from a wall of the hole through the material and a method of sampling the material under a strata.

35 Claims, 9 Drawing Sheets

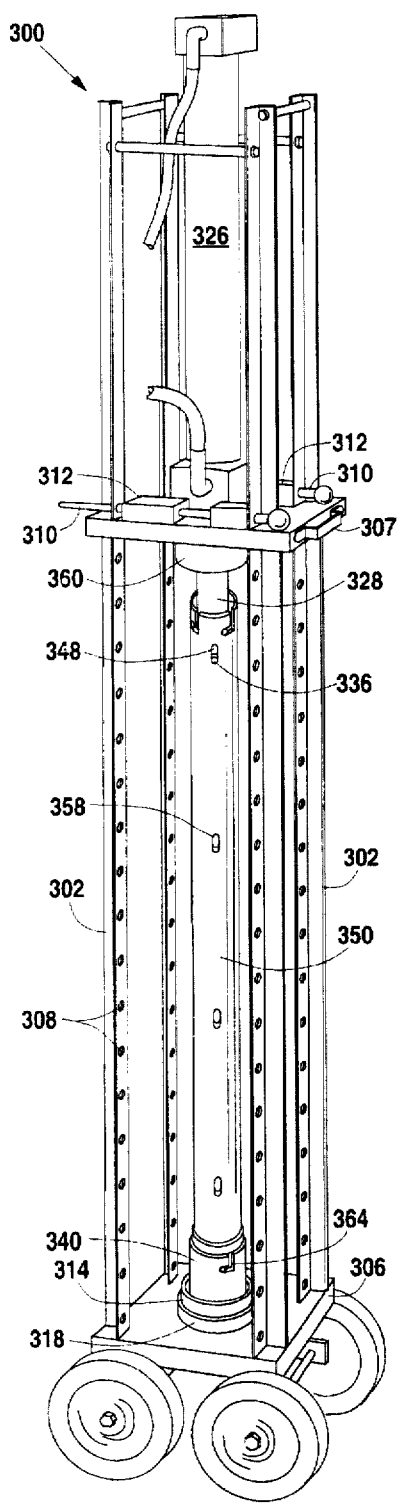
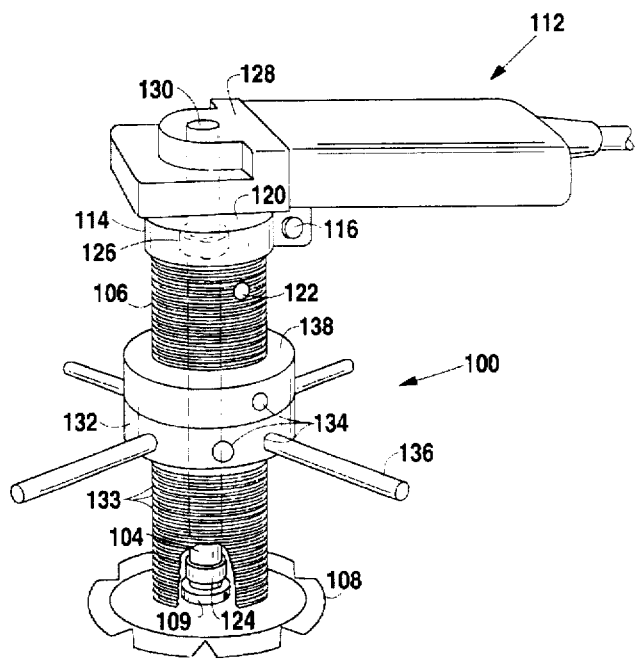
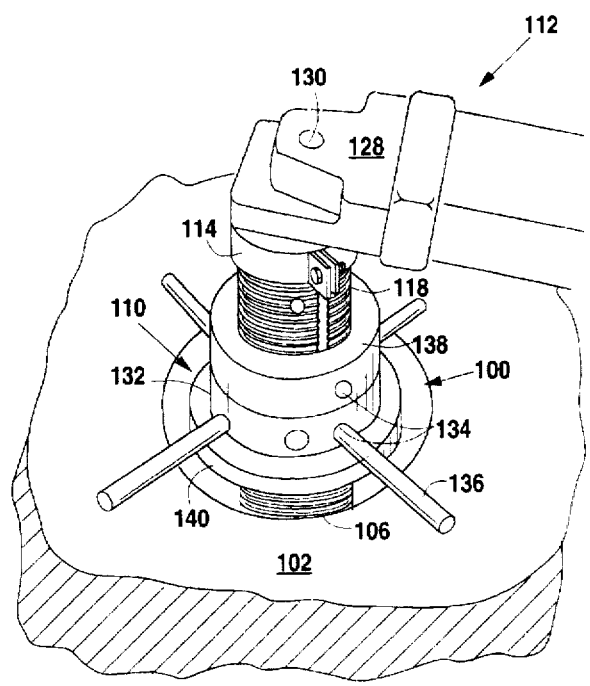
Fig. 11
Fig. 1
Fig. 2

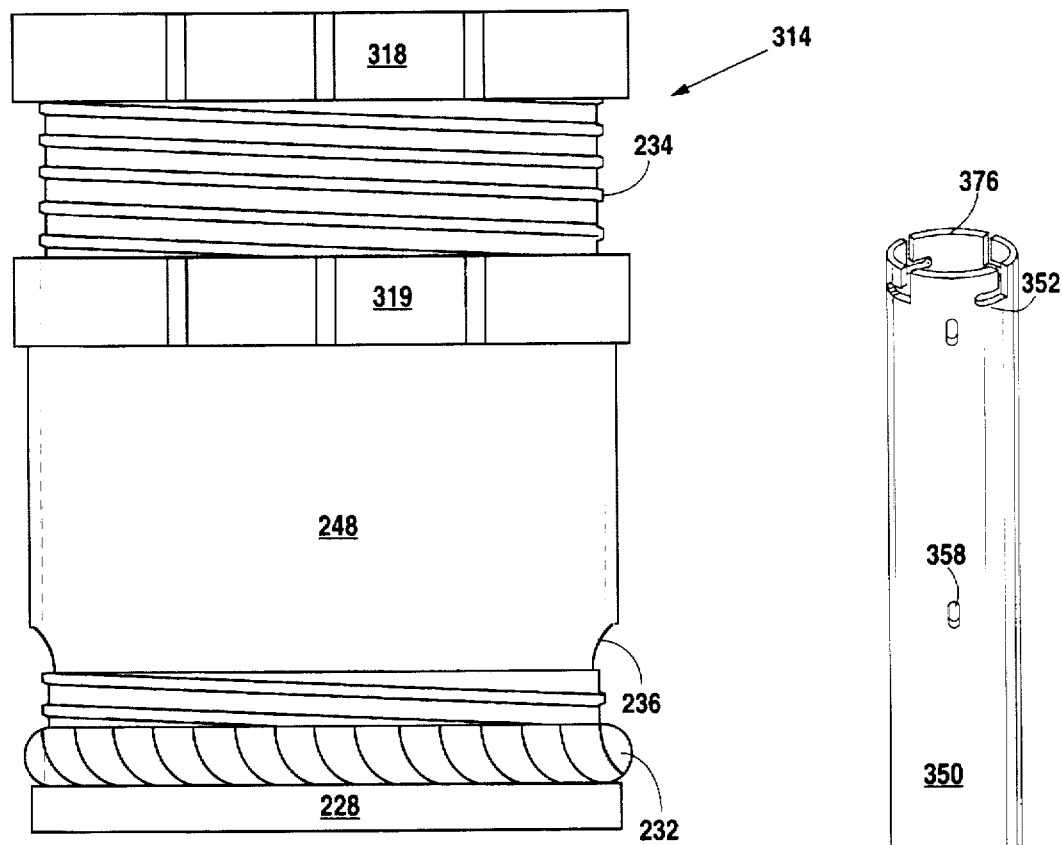
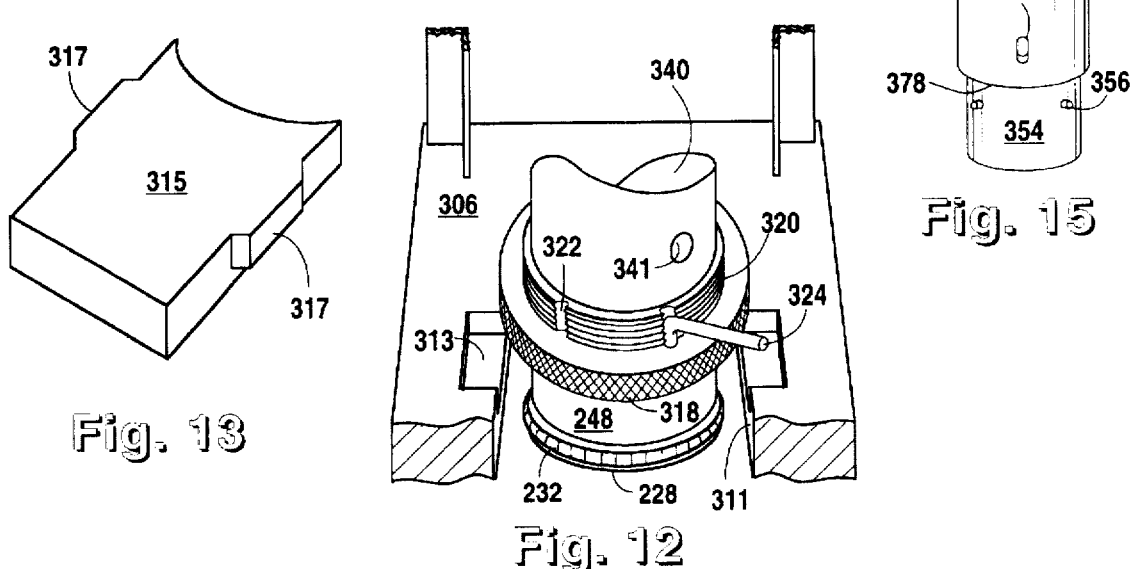

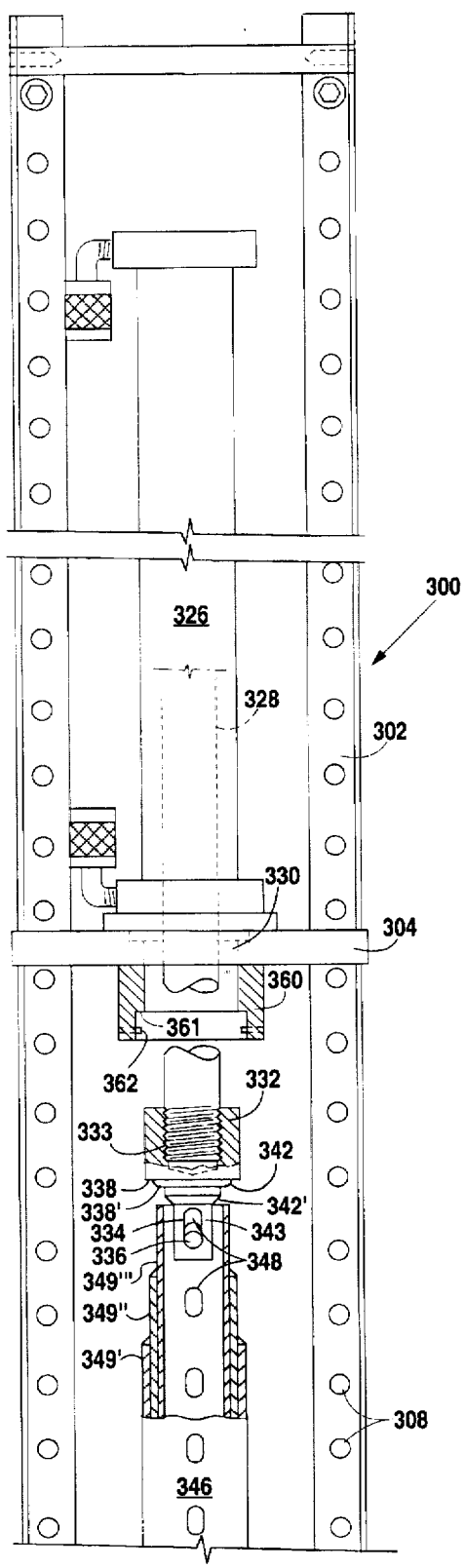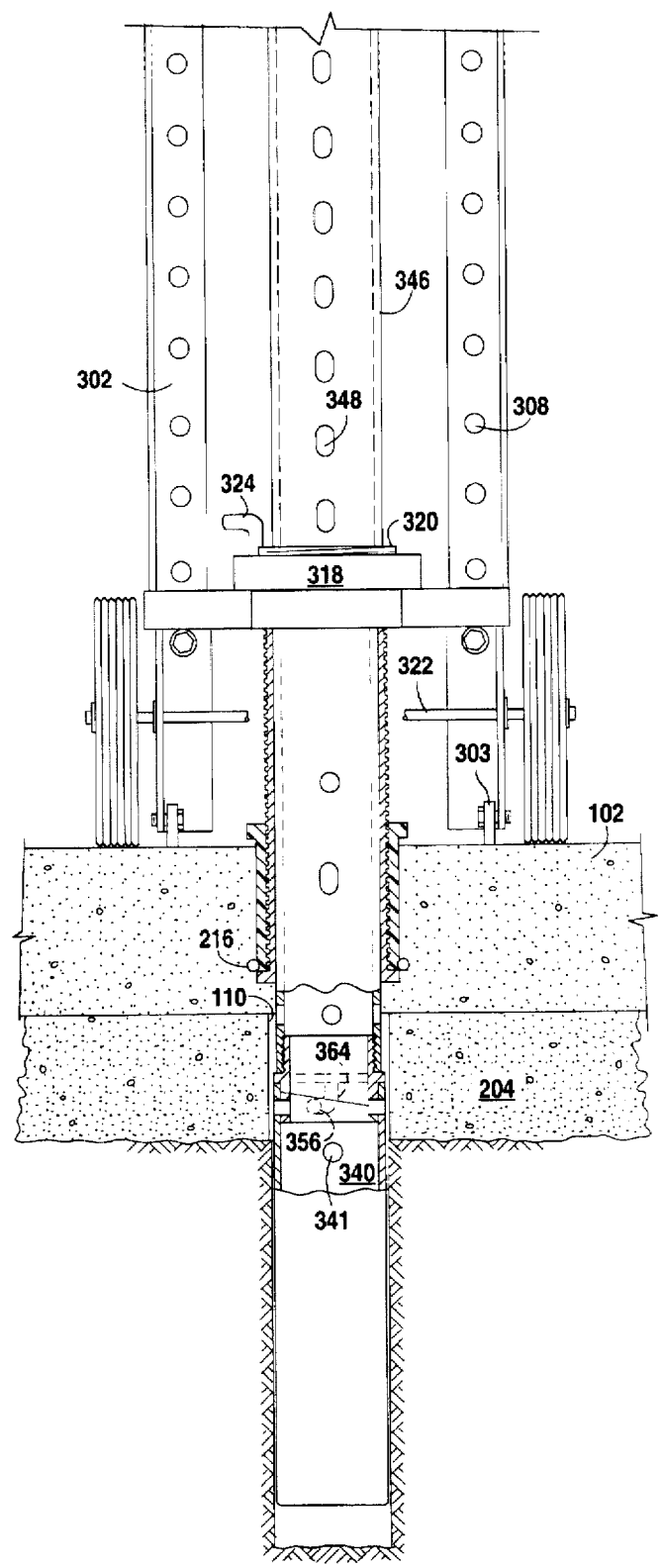
Fig. 14A1    Fig. 14B1

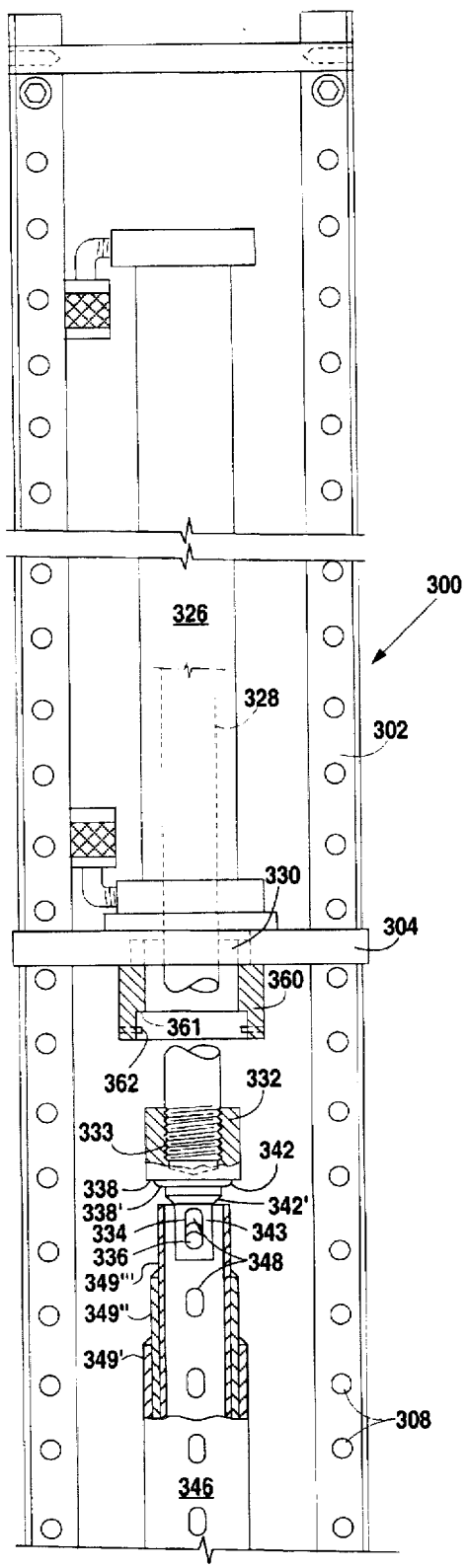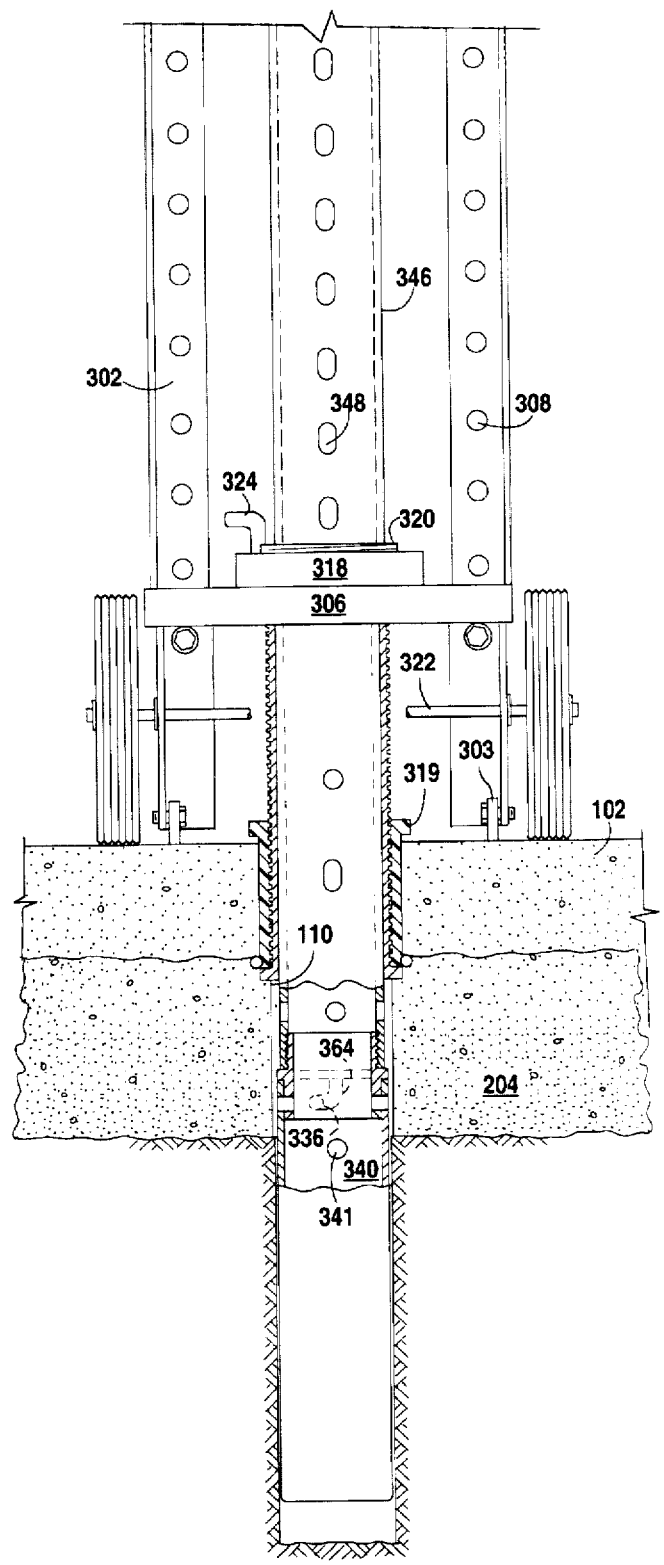
Fig. 14A2    Fig. 14B2

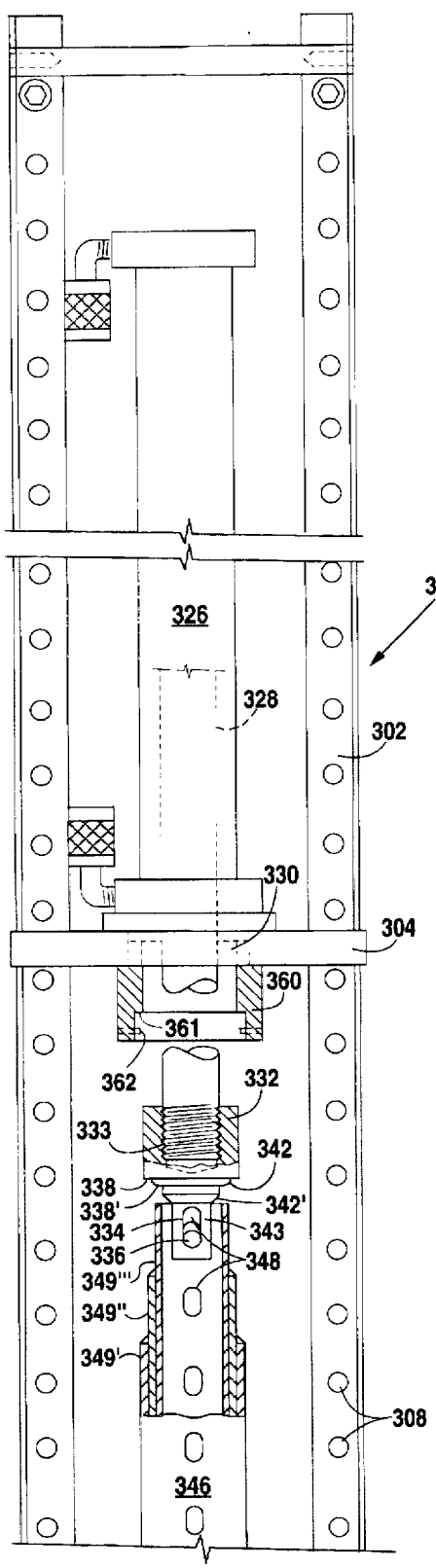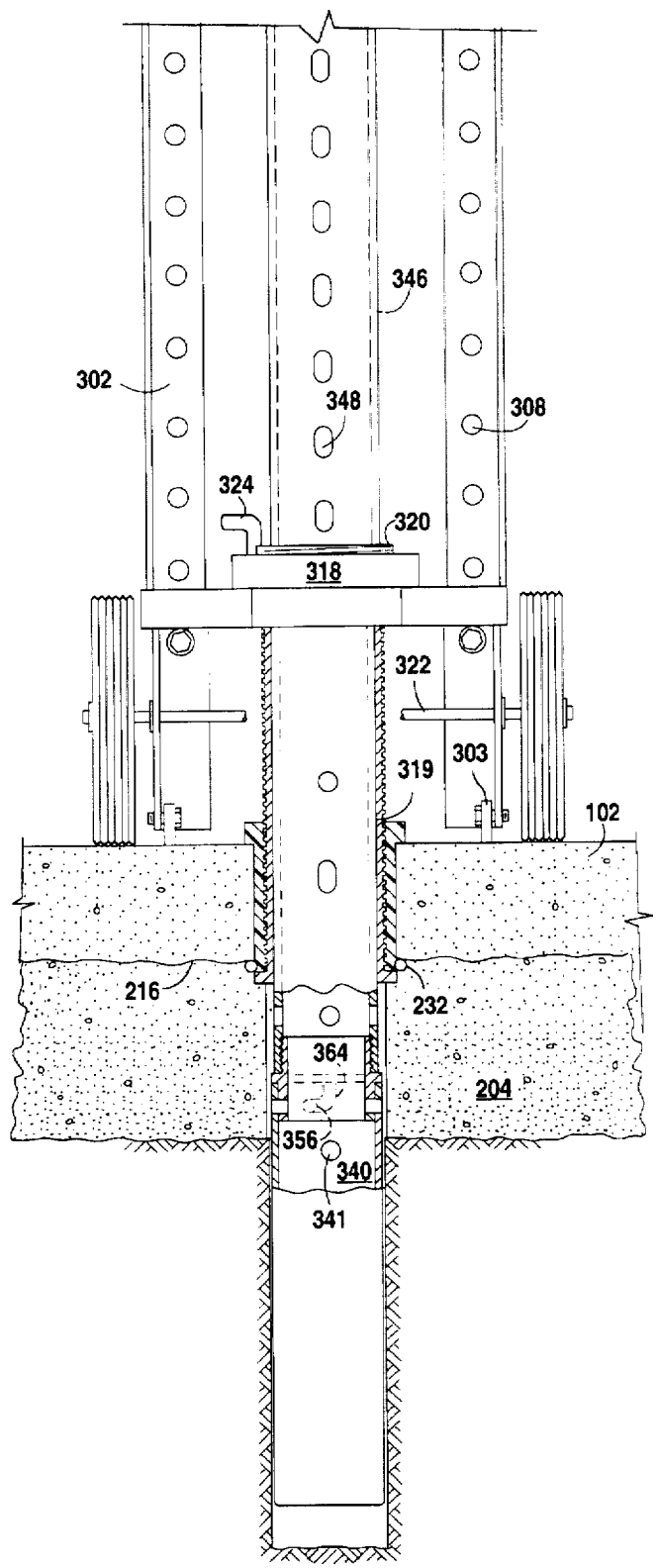
Fig. 14A3    Fig. 14B3

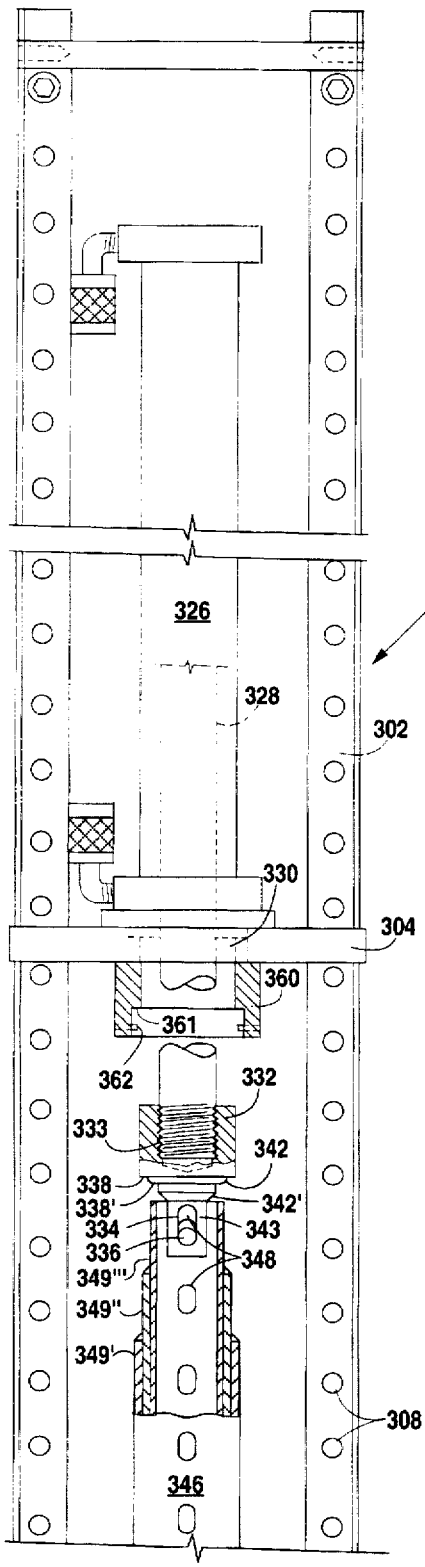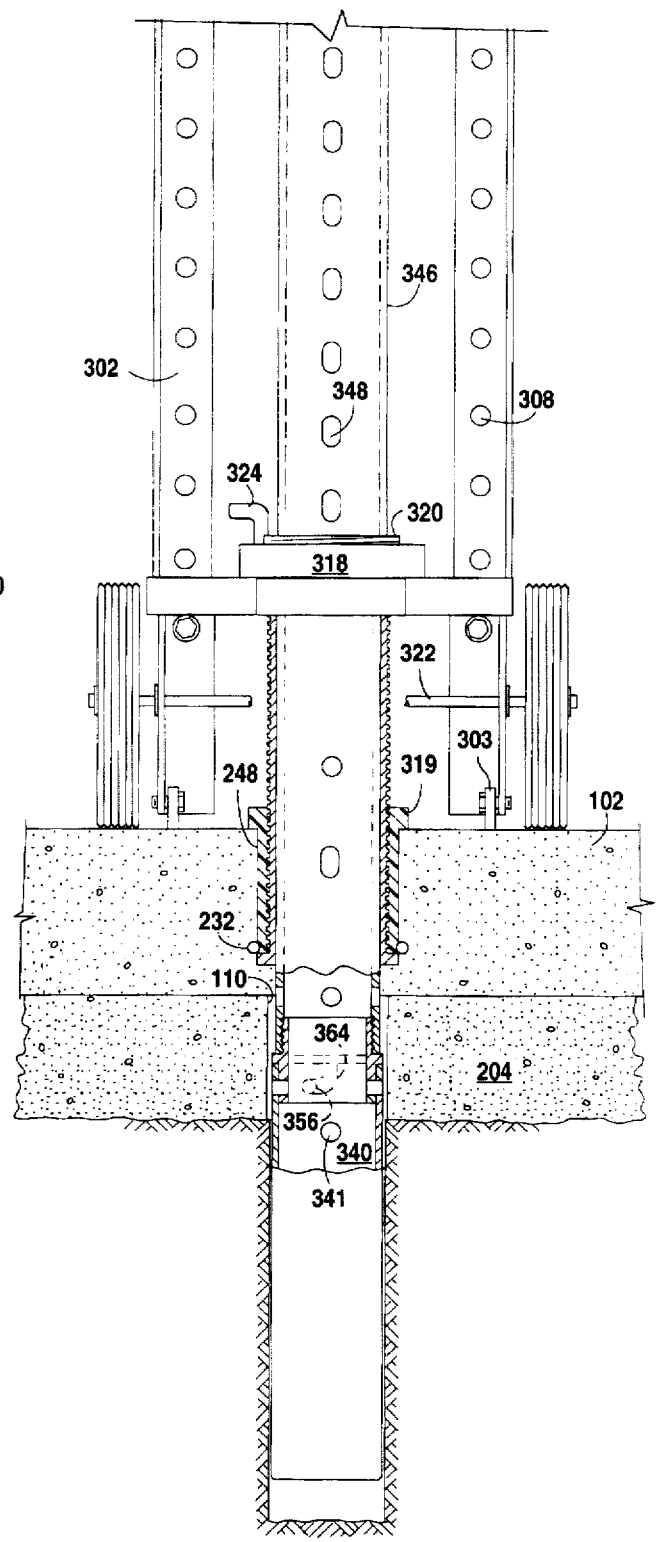
Fig. 14A4  Fig. 14B4

METHOD AND APPARATUS FOR REMOVING MATERIAL FROM A HOLE IN A STRATA FOR USE IN FORCING A MEMBER INTO MATERIAL COMPRISING OR UNDERLYING THIS STRATA

CROSS REFERENCE TO RELATED APPLICATION

This application is a continuation-in-part of my application Ser. No. 08/393,507, filed Feb. 23, 1995 and entitled PROVIDING REACTIVE FORCE ANCHORAGE FOR SUCH AS SOIL AND OBTAINING SAMPLES THEREFROM. Ser. No. 08/393,507 is a continuation of abandoned application Ser. No. 08/304,804, filed Sep. 12, 1994 and having the same title as Ser. No. 08/393,507. Ser. No. 08/304,804 was itself a continuation of application Ser. No. 07/815,064, filed Dec. 27, 1991 and entitled METHOD AND APPARATUS FOR FORCING A MEMBER THROUGH MATERIALS SUCH AS SOIL AND OBTAINING SAMPLES THEREFROM, which is now abandoned. Ser. No. 07/815,064 was a continuation-in-part of application Ser. No. 07/581,181 of the same title filed on Sep. 10, 1990 and now issued as U.S. Pat. No. 5,076,392. Ser. No. 07/581,181 was filed as a continuation of application Ser. No. 07/250,321, filed Sep. 28, 1988 and having the same title as Ser. No. 07/581,181, and which is now abandoned.

BACKGROUND OF THE INVENTION

The present invention relates to an apparatus and method for forcing a member through a material, especially where such materials exist in conjunction with a load bearing strata, either naturally occurring or man-made, and which transmits the reactive forces developed during use of the invention either to the material or to the load bearing strata. More particularly, the present invention relates to (1) a method and apparatus for obtaining material samples, such as soil samples, from within the material or from a material underneath, behind or overlying a structure or concrete slab and (2) a method and apparatus for creating a discontinuity in the load bearing strata or the material from which a sample is being taken.

A common work activity of geotechnical scientists and engineers is the analysis and evaluation of material deposits. For example, when a building structure has experienced distress to its foundation or to other elements of construction, information concerning the soils and other materials underlying the structure, as well as physical samples of those materials, is required for the analysis and evaluation of the distress.

It is well known in the geotechnical field that such samples should be "undisturbed" because sample disturbance increases the likelihood and degree of error in the assessment of the in situ physical properties and characteristics of the material sampled. "Undisturbed" samples are commonly obtained by advancing a thin-walled tube, ranging in length from several inches to several feet and commonly called a "Chicago Tube" or a "Shelby Tube", into the soil or other material to be sampled. Once the tube is sufficiently advanced to contain a "plug" of the material to be sampled, it is withdrawn. That operation is repeated a sufficient number of times, using a number of such tubes, to create a continuous series of sample "plugs" which comprise the physical "undisturbed" samples of the materials through which the sample tube is forced. Upon completion of the sampling and retrieval operations, the plugs of soil are removed from the tubes and various tests performed to assess the properties of the material samples.

Although it is sometimes fairly easy to obtain such samples with truck-mounted conventional drilling and sampling equipment, such equipment is relatively expensive to purchase and operate, and in many cases, space and other limitations prevent the entry of a relatively large, truck-mounted drilling rig into the location at which sampling must be conducted. Limitations of that nature are particularly acute when the sampling site happens to be within a building or other structure, for instance, when information might be required about the materials under a foundation slab after the slab has shifted or cracked. In such cases, the size of the truck-mounted drilling rig and the fumes produced by the truck's motor obviate its use and require the use of cumbersome hand-sampling methods (described below).

Presently-utilized hand-sampling methods generally involve manually impact-driving the sample tubes into the sub-foundation materials with sledgehammers or drop-weights. The sample tubes are generally attached to the end of a piece of pipe or other suitable rod for driving and, after being so driven, are extracted by manually impacting them out of the "hole" or, in some cases, using automobile jacks to jack against chains which are wrapped around the sample tube drive rod. After the samples are retrieved, they are extruded from the sample tube at a standby drill rig having extrusion capability or they are taken back to a laboratory for extrusion.

As is well known to those skilled in the art, the disadvantages of such hand-sampling techniques and equipment are many. They include, for instance, the extremely labor and equipment intensive nature of the techniques and difficulty, or even impossibility, of obtaining samples as the hardness of the sub-foundation materials increases. From an economic standpoint, only shallow samples can be obtained, and the tendency of the axis of advancement (or retraction) to wander (especially in harder materials) introduces additional variables into assessment of the samples and increases the amount of effort required. Further, even though the samples are supposed to be "undisturbed" samples, they are often severely disturbed due to the impacts required to advance and retract the sample tube. Sample quality is, therefore, unpredictable and erratic, worker fatigue is common and can be extreme. An additional limitation of such techniques is that they cannot be used to place various members or device, such as penetrometers, stepped blade soil pressure transducers, piezometer tubes, soil gas samplers and bore hole dilatometers for example, into the material for in situ assessment of the properties of the material because of the cumbersome nature of such techniques and the sensitivity of such members or devices to the impacts needed to advance them into the materials.

Although the above discussion refers in large part to methods for obtaining samples from beneath structures, the problems and limitations discussed are generally similar to those encountered whenever it is desired to advance or retract a device or member through a mass of material. Such operations are common in the geophysical, geological, environmental monitoring, and construction arts and include, but are not limited to, driving and the placement of members such as sampling electrodes, benchmarks, geophysical logging equipment, well points, well casings, and soil anchors for guy wires and retaining walls, as well as the penetrometers, pressure transducers, piezometer tubes, and soil gas samplers discussed above. It is, therefore, an object of the present invention to provide an apparatus which is adaptable for a number of purposes relating to advancing and retracting such a member or device(s) within a mass of material such as soil.

Further, although the above discussion refers primarily to performing an operation such as obtaining a soil sample from beneath a building foundation, it will be understood that the structure need not be a building-foundation. Indeed, it is another object of the present invention to provide a small, portable device for forcing a member or device through a mass of material and which transmits the reactive forces resulting from the resistance of the material to the forcing of the member therethrough to the material or to a load bearing strata such as a concrete drain culvert, retaining wall, a naturally occurring rock foundation or other strata, or the strata itself comprising the material through which the member is to be forced, as well as a floor, slab, foundation, or other elements of a building.

Further, so far as is known, no practical device or method is available for performing such operations on steeply sloped or overhead surfaces, or in enclosed or confined spaces. It is another object of the present invention to provide such an apparatus.

A further object of the present invention is to provide an apparatus which can be used to obtain tube-type soil or material samples and to extrude those samples from the sample tube on-site, thus obviating the need for extrusion of the sample from the sample tube with a standby drill rig or at the lab, thereby enhancing the scientist's ability to direct an effective sampling program in the field.

It is another object of the present invention to provide an apparatus which can penetrate hard formations that hand-sampling methods cannot breach, can be adapted for setting benchmarks and their casings without the requirement of first drilling a pilot shaft, and can be utilized to place, or advance or retract, various devices and instruments, including, but not limited to, piezometer tubes, ditch cone penetrometers, other types of probes or bits, soil anchors, and soil pressure meters in the soil, as well as soil or other material sampling.

The advantages of such a device will be apparent to those skilled in the art from even the above-summarized brief description of the various uses and capabilities of the present invention. In short, the apparatus and method of the present invention saves time and money, eliminates manual hammer and drop weight methods, allows work in confined locations or locations that are otherwise inaccessible to conventional power equipment, and reduces the size of the crew required for performing the on-site operations necessary for the scientist or engineer to attain his or her objectives. The member can also be advanced further into the mass of materials than is currently possible with hand methods. Because the member, notably a sample tube, is smoothly forced straight into the materials worked upon, the undesirable effects of impacting, sample disturbance, and wandering of the axis of advancement are reduced. Operator fatigue is reduced and sample extrusion can be handled on-site.

SUMMARY OF THE INVENTION

To achieve the above-described objects and advantages, an apparatus is provided for forcing a member or device through a material comprising means for selecting the line of action along which a member is to be forced through a material, means mounted to the line of action selecting means for forcing the member through the material along the line of action when activated, and means for positively engaging the material through which the member is to be forced having an opening therethrough for passage of the member when the member forcing means is activated. Means is mounted to the line of action selecting means for engaging the material engaging means to transmit the reactive forces resulting form the resistance of the material to the forcing of the member therethrough upon activation of the member forcing means to the material.

The means for transmitting reactive forces to a strata or material resulting from the exertion of force along a line of action at an angle with respect to the strata or material comprises, in a presently preferred embodiment, a locking dog for inserting into a hole in a strata to be sampled or other suitable load bearing strata and having an outer surface that is threaded along the length thereof and provided with a shoulder at one end thereof. The locking dog is also provided with means mounted on the threads for engaging an apparatus for exerting force along a line of action at an angle with respect to the strata to be sampled and means resting on the shoulder for engaging or creating a groove or discontinuity in a hole in the strata to transmit the reactive force developed by the force exerting apparatus to which the locking dog is engaged to the material or strata when forced outwardly by movement of means moveable along the threads for that purpose.

An additional aspect of the present invention is directed to an apparatus for removing material from a hole in a strata comprising a drive shaft rotatably mounted within a housing having a cutting blade mounted on one-end thereof for removing material from a hole in a strata, the other end of the drive shaft being adapted for engaging power means for rotating the drive shaft. Means for supporting the housing over the hole in the strata with the cutting blade extending into the hole is movably mounted on the outside of the housing. The depth to which the cutting blade extends into the hole can be changed by movement of the supporting means relative to the housing. Means is also provided for selectively preventing the movement of the supporting means relative to the housing to maintain the cutting blade at a selected depth in the hole and to control the amount of material removed.

In another aspect of the present invention, there is provided an apparatus for obtaining a soil sample. The apparatus comprises a derrick for selecting a line of action resting on a load bearing strata and having upper and lower plates mounted to the legs thereof, with a means for forcing a sample tube downwardly into the soil under the load bearing strata mounted to the upper plate. Means having an opening therethrough for passage of the sample tube when the forcing means is activated is mounted to the lower plate for positively engaging the load bearing strata to transmit reactive forces resulting from the resistance of the soil to the forcing of the sample tube therethrough upon activation of the forcing means to prevent movement of the derrick with respect to the load bearing strata.

BRIEF DESCRIPTION OF THE DRAWINGS

FIG. 1 is a perspective view of an apparatus constructed in accordance with the present invention for removing material from a hole in a strata.

FIG. 2 is a perspective view of the apparatus of FIG. 1 in use for material removal operations and having means for changing the depth of the groove mounted thereto.

FIG. 8 is an elevational side view of an apparatus constructed in accordance with the present invention for transmitting reactive forces to a strata that are exerted along a line of action at an angle with respect to the strata.

FIG. 11 is a perspective view of an apparatus constructed in accordance with the present invention for forcing a member through a material.

FIG. 12 is a perspective view of a portion of the apparatus of FIG. 11.

FIG. 13 is a perspective view of the closure plate for use in connection with the apparatus of FIG. 11.

FIGS. 14A1 and 14B1 are partial, longitudinal sectional views of the apparatus of FIG. 11 showing the apparatus forcing a member through a material. FIGS. 14A2 and 14B2, 14A3 and 14A3, and 14A4 and 14B4 show different embodiments of the manner in which either the slab or other material into which the reactive forces are to be transferred are positively engaged.

FIG. 15 is a perspective view of an alternative embodiment of a force transmitting means for mounting on the apparatus of FIG. 11.

DETAILED DESCRIPTION OF THE INVENTION

Figure 3:
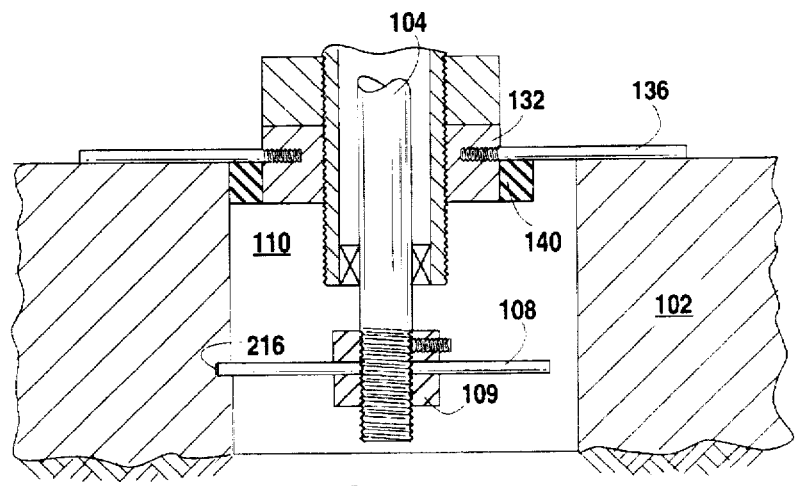
FIG. 3 is a sectional view of the apparatus of FIG. 2.

The present invention can best be understood by referring first to FIGS. 1, 8, and 11, in which each of an apparatus for removing material from a hole in a strata, an apparatus for transmitting reactive forces exerted along a line of action at an angle with respect to a load bearing strata to the strata, and an apparatus for aligning and forcing a member through a material is indicated generally at reference numerals 100, 314, and 300, respectively. The apparatus 100 shown in FIG. 1, which may be conveniently referred to as a groover tool, is shown in use for grooving the wall of a hole 110 in a strata 102 in FIG. 2. The apparatus 314, which may be referred to as a locking dog, is shown in place in a hole 110 in a strata 102 in FIG. 14B, and transmits reactive forces to strata 102 regardless of the direction in which they are exerted. The apparatus 300, which may be conveniently referred to as a derrick, is shown in FIG. 11 and in sectional view engaging locking dog 314 in FIGS. 14A and 14B.

Referring first to the groover tool 100 shown in FIGS. 1 and 2, groover tool 100 is comprised of a drive shaft 104 rotatably mounted within an elongate, hollow housing 106 and having a cutting blade 108 mounted on one end thereof for removing material from a surface such as the wall of the hole 110 or the surface of a load bearing strata 102 as shown in the alternative embodiment shown in FIG. 4 as will be described. The other end of drive shaft 104 is adapted for engaging power means, indicated generally at reference numeral 112, for rotating drive shaft 104 in housing 106. Power means 112 can be any source of power such as a hand held electrical motor and gear assembly as shown in FIGS. 1 and 2, an electric drill, or other device provided with suitable means for connection to drive shaft 104 as is known in the art. In the embodiment shown, a band clamp 114, having a screw 116 therein, is provided around the housing 106 for insuring a secure connection between power means 112 and housing 106. A slot 118 is cut longitudinally into a portion of housing 106 to allow the slip fit of housing 106 over hub 120 of power means 112. Upon proper fit, screw 115 is tightened, tightening clamp 114 around hub 120, and compressing housing 106 to positively engage power means 112. An opening 122 is provided through the wall of housing 106, and drive shaft 104 is provided with a similar hole (not shown) co-incident with opening 122, for receiving a pin (not shown) or other elongate member for selectively preventing rotation of drive shaft 104 relative to housing 106 to facilitate, for instance, the changing of cutting blade 108 when the retaining nut 109 holding blade 108 into shaft 104 is removed. Cutting blade 108 is a conventional diamond tipped abrasive blade or any other suitable material removal or cutting means as is known in the art.

As will be described below in connection with the description of the use of the groover tool 100, side thrust forces are developed on drive shaft 104 and cutting blade 108. Those side thrust forces are resisted by bearings 124 and 126 at the ends of housing 106.

The gear box 128 is provided with a hole 130 aligned with the axis of drive shaft 104 for receiving and conveying water, compressed air, or other working fluid to cutting blade 108 for cooling the blade and the surface from which material is being removed, lubricating and reducing the dust and noise produced during removal of the material.

Figure 4:
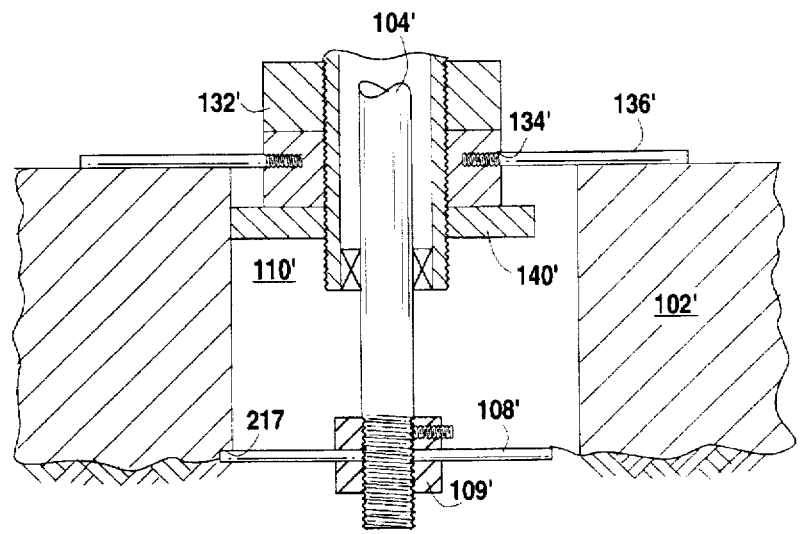
FIG. 4 is a sectional view similar to that of FIG. 3 showing an alternative embodiment for mounting the means for changing the depth of the groove to the apparatus of FIG. 2.

As shown in FIGS. 2–5, groover tool 100 is inserted into the hole 110 in strata 102 to rout out material from the inside surface of the hole 110 therein (FIGS. 3 and 5) or from the bottom of strata 102 (FIG. 4). Groover tool 100 is provided with means for locating the point at which cutting blade 108 is to perform material removal operations mounted on the outside surface of housing 106 in the form of a locating lug 132 having a plurality of spokes 136 extending outwardly therefrom and which is carried by the threads 133 of housing 106. Jam nut 138 is also threaded onto the outside of housing 106 and provides a means for selectively preventing movement of lug 132 with respect to housing 106, thus preventing a change in the depth of cutting blade 108, i.e., by snugging jam nut 138 up against lug 132. Spokes 136 are received within the holes 134 on both lug 132 and jam nut 138 as, for instance, by screw threads, and can be conveniently used as a means for exerting leverage to securely snug jam nut 138 to lug 132 to prevent rotation of lug 132 with respect to housing 106 and to break jam nut 138 apart from lug 132 when it is desired to change the depth at which material removal operations are to be conducted. Alternatively, housing 106 is provided with a track, slot, or groove running along the length thereof (not shown) in place of the threads 133 having a plurality of detents therein and the locating lug 132 is provided with a set screw (not shown) which is tightened so as to engage one of the detents to retain the lug 132 at a selected location on the housing 106, thereby setting the depth at which material removal operations are conducted. Spokes 136 extend outwardly from lug 132 a sufficient length to support the housing 106 over the opening of hole 110 in strata 102 as shown in FIG. 2 and to facilitate material removal operations by supporting cutting blade 108 in a plane perpendicular to the surface of hole 110. In other words, material is removed from the strata 102, or from the material 102" (see FIG. 5 and the corresponding description set out in the next paragraph and in conjunction with FIG. 5), on a plane which is substantially parallel to the surface of the strata 102 (or 102") on which the spokes 136 (or 136") rest. As will be apparent to those skilled in the art who have the benefit of this disclosure, other means (not shown) can be provided for supporting groover tool 100 over hole 110, for instance, a plate extending outwardly from either lug 132 or jam nut 138. The use of such a plate has the advantage of reducing the amount of dust and debris emerging from hole 110 during material removal operations.

Cutting blade 108 extends down into hole 110 to a location which is controlled by the position of spokes 136 in relation to cutting blade 108. The location can be changed by loosening jam nut 138, rotating lug 132 relative to housing 106, and then snugging jam nut 138 to lug 132. As noted above, in another preferred embodiment, the location can also be controlled by use of structure such as a track having position detents and a set screw for engaging one of the detents when tightened that is located on lug 132. Although cutting blade 108 has been described as extending down into hole 110, it will be understood by those skilled in the art who have the benefit of this disclosure that hole 110 need not necessarily extend downwardly or even exist in a strata such as a concrete slab. Groover tool 100 will function satisfactorily to remove materials if held against the strata 102 in whatever orientation the strata 102 presents, whether strata 102 is horizontal, vertical or overhead, and regardless of the type of strata, e.g., rock, clay, caliche, concrete, and so on, and regardless of whether a concrete slab is present (see, for instance, FIG. 5). In addition, hole 110 need not have an axis which is perpendicular to the surface of strata 102.

Nor is removal of materials with groover tool 100 limited to the forming of a groove. Material removal can also be conducted, for instance, on the underside of strata 102 around hole 110 when it is desired to level the bottom surface of a concrete slab to provide a bearing surface for other elements of the invention, as will be described below in connection with the description of FIG. 4. Material need not be removed continuously around the wall of the hole 110 or the bottom surface of the strata 102 as will be apparent from the discussion of an alternate embodiment of the groover tool 100 and locking dog 314, infra.

Removal of material, for instance routing out a groove in the surface of the wall of hole 110, is performed by forcing cutting blade 110 against the surface from which material is to be removed while drive shaft 104 is rotated by power means 112. The groove is extended around the circumference of the wall of hole 110, to the extent it is desired to do so, by sliding groover tool 100 around on the surface of strata 102 on spokes 136 until the outer surface of locating lug 132 encounters the wall of the hole 100. To further control the depth of the groove in the wall of hole 110, a cutting depth control ring 140 (see FIGS. 2 and 3) of selected surface is pressed onto the outer thickness of the locating lug 132, thereby decreasing the amount of material removed from the inside wall of hole 110, e.g., the diameter of discontinuity or depth of groove 216, is reduced. Controlling the amount of material removed from the surface of hole 110 reduces the time needed for that operation to the maximum extent possible while allowing the radially extensible member 232 of locking dog 314 (see FIG. 14B) to be securely fitted into that discontinuity or groove 216. Radially extensible member 232 in the embodiment shown is a helically wound spring which has the ends joined to form a circular shape to fit locking dog 314 as is explained in more detail infra. Further, as will be made clear below, certain advantages of the present invention are enhanced if the amount of material removed is limited. In one embodiment, depth control ring 140 is comprised of a resilient and/or slightly elastic material and is provided in a variety of thicknesses for achieving controlled amounts of material removal.

Figure 5:
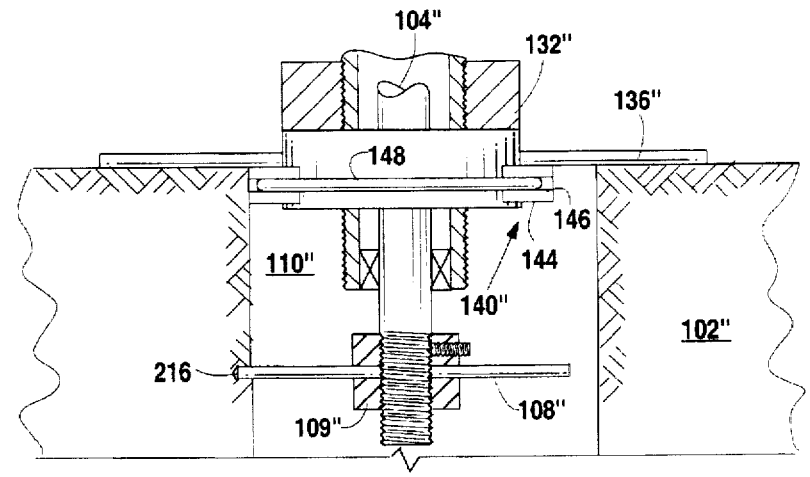
FIG. 5 is a sectional view similar to FIG. 3 showing yet another alternative for mounting the means for changing the depth of the groove to the apparatus of FIG. 2.

Referring to FIGS. 4 and 5, alternative embodiments of the depth control ring shown at reference numeral 140 is FIG. 3 are shown using the same reference numerals and the "prime" designation, where possible, to refer to similar parts. Referring first to FIG. 4, depth control ring 140' is sized to fit snugly against the housing 106' rather than the outside surface of locating lug 132'. In the case of both depth control ring 140 and depth control ring 140', the depth of discontinuity 216 or 216' is achieved by varying the thickness of depth control ring 140 or 140'. Depth control ring 140' is also used in the same manner as jam nut 138, e.g., to prevent rotational movement of lug 132, thereby obviating the need for jam nut 138. Although groover tool 100 is used in any of the embodiments shown in FIGS. 3–5 to level the bottom surface of a strata 102 such as concrete slab, such a use is illustrated only in FIG. 4. Depth control ring 140' (or 140", see below) functions in the same manner when the apparatus is used for this purpose; the difference is that instead of a groove 216 (see below), a flat surface 217 results. Referring to FIG. 5, the depth control ring 140" is comprised of a plurality of semi-circular members, such as those shown at reference numerals 142 and 144, having a longitudinal groove 146 therein. Semi-circular members 142 and 144 are applied to the outside surface of locating lug 132" and held there by means of the extensible member 148 which rests in the groove 146 in members 142 and 144. Extensible member 148 can be an elastic or rubber O-ring or a radially extensible member such as previously described. The amount of material removed, e.g., the depth of groove 216" routed out in the wall of hole 110', is controlled by using semi-circular members 142 and 144 of different thicknesses. Semi-circular members 142 and 144 can also be applied to and held on the outside surface of lug 132" magnetically or in other ways known in the art.

Figure 6:
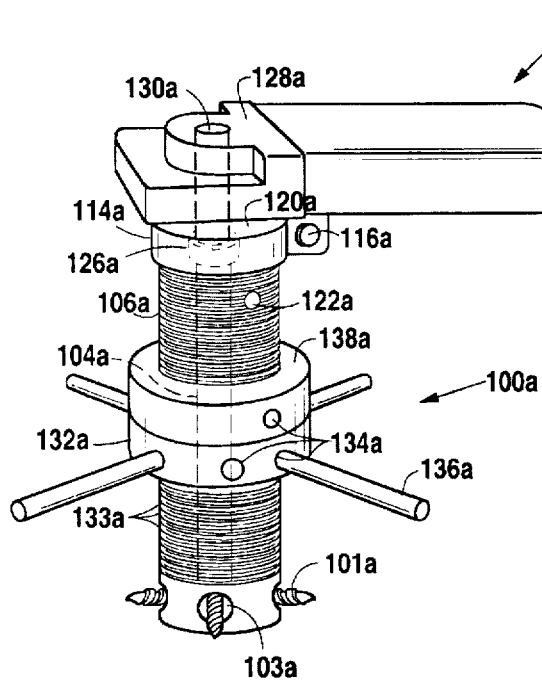
FIG. 6 is a perspective view of an alternative embodiment of the apparatus of FIG. 1.

Another embodiment of the groover tool of the present invention is shown in FIG. 6. As noted above, it is not necessary to remove material from the wall of the hole 110 all the way around the hole, and the embodiment shown in FIG. 4, indicated generally at reference numeral 100a, is intended to provide a discontinuity such as described infra in the wall of the hole 110 (not shown in FIG. 6) which does not extend all the way around the wall of the hole. Instead, groover tool 100a is provided with a plurality of drill bits 101a extending radially outwardly from the housing 106a through holes 103a in housing 106a. Each of the bits 101a is driven by a planetary gear (not shown) forming a right angle drive off of the drive shaft 104a. All other components of the groover tool 100a are the same as the corresponding parts of the groover tool 100 shown in FIGS. 1 and 2, are labelled with an "a" designation on the corresponding reference numerals, and therefore need not be explained in detail here. As will be explained in connection with the description of locking dog 314a (FIG. 10), intended for use in connection with groover tool 100a, groover tool 100a is used to make four radially-spaced holes in the wall of a hole in the load bearing strata.

Figure 7:
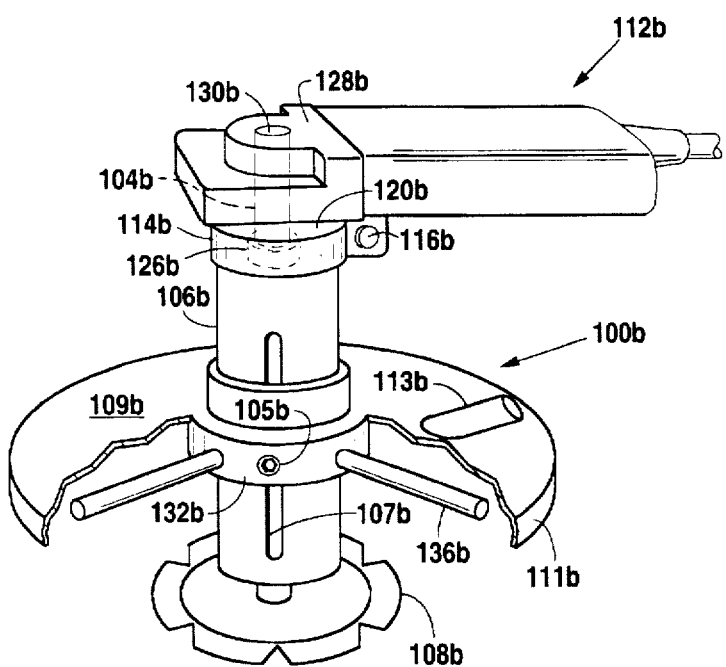
FIG. 7 is a perspective view of a third alternative embodiment of the apparatus of FIG. 1.
Figure 9:
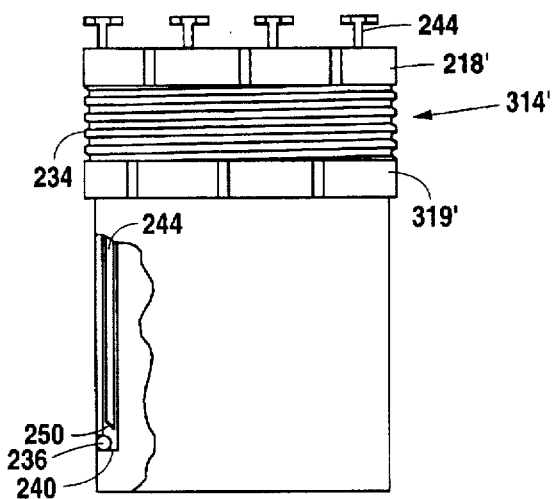
FIG. 9 is an elevational side view of an alternative embodiment of the apparatus of FIG. 8.

A third embodiment of the groover tool of the present invention is shown in FIG. 7. Like the groover tool 100

(FIGS. 1 and 2), groover tool 100b (FIG. 7) is driven by power means 112b, which turns drive shaft 104b to which the blade 108b is mounted in the same manner as described above in connection with groover tool 100 (FIGS. 1 and 2). Groover tool 100b is provided with a locating lug 132b having a plurality of spokes 136b extending outwardly therefrom and which is carried on the outside surface of housing 106b. A set screw 105b in lug 132b is used to set the depth of cut of the blade 108b, the set screw 105b sliding up and down the housing 106b in the slot 107b cut therein to prevent rotation of the lug 132b during cutting operations. Lug 132b is also provided with a shroud 109b, shown partially cut away in FIG. 7 to show the set screw 107b and spokes 136b, having a lip 111b around the outer periphery thereof which extends downwardly over the ends of spokes 136b. The shroud 109b is also provided with a nozzle 113b sized for attachment to a vacuum cleaner hose (not shown). During cutting operations, the shroud 109b reduces the dust and dirt which are otherwise thrown about and attaching a vacuum cleaner to the nozzle 111b effectively eliminates the dust. The slip fit of the shroud 109b around housing 106b allows the use of the vacuum cleaner during cutting operations because the shroud 109b does not rotate. Other component parts of groover tool 100b are the same as the corresponding parts of groover tool 100 and are numbered with the same reference numerals and the "b" designation.

Those skilled in the art who have the benefit of this disclosure will recognize that the lip 111b and nozzle 113b are not necessary for reducing dust and that there may be situations in which it is desirable to use a shroud without these features. For instance, more air can be sucked under the shroud by the vacuum cleaner if the shroud is not provided with the lip 113b. Increased air flow not only increases the ability of the vacuum cleaner to suck up dust but also has the advantage of allowing the vacuum cleaner to run cooler since many vacuum cleaners use their suction air for cooling. In one embodiment (not shown) the outer periphery of the shroud is provided with a strip of downwardly-extending bristles which allow passage of air down into the hole in which material removal operations are being conducted but prevent the escape of dust therefrom.

One unexpected advantage of the use of the shroud 109b having the downwardly-extending lip 113b formed around the outer periphery thereof is that operation of the vacuum cleaner during material removal operations actually creates a vacuum in the hole in which material removal operations are being conducted. The vacuum is sufficient to cause atmospheric pressure bearing on the top surface of shroud 109b to help stabilize the groover tool 100b during material removal operations. To improve the sealing effect of the edge of lip 113b against the surface on which the spokes 136b rest during material removing operations, the lip 113b may be provided with an elastomeric seal or skirt (not shown).

Referring now to FIG. 8, locking dog 314, which comprises a means for positively engaging the material such as the strata 102, or the soil 204 through which a member is to be forced, will be described in detail. In a presently preferred embodiment, locking dog 314 is a right circular cylinder and is therefore shaped to accommodate the hole 110 in the load bearing strata 102 being a round hole such as would be drilled through a concrete floor slab or other strata with a conventional core drill (not shown). However, it will be recognized by those skilled in the art who have the benefit of this disclosure that hole 110 need not be round, and locking dog 314 need not have a rounded outer surface for the locking dog 314 to function for the intended purpose of resisting the reactive forces which cause movement either way from or down into strata 102 when force is applied thereto. All that is required is that the outer surface of the locking dog 314 provide sufficient support for the engagement means 232 for engaging the wall of the hole 110 in strata 102, and generally, the more closely the shape approximates that of the hole 110, the better the ability of locking dog 314 to transmit forces exerted thereon to strata 102.

Locking dog 314 is provided with means for engaging an apparatus for exerting force along a line of action at an angle with respect to the strata in which the hole is located to force a member through a material such as the derrick 300 shown in FIGS. 11 and 14. The locking dog 314 is provided with threads 234 along the length of the outside surface and has a shoulder 228 formed at one end thereof. The locking dog 314 uses a radially extensible member 232, resting on the shoulder 228 of the locking dog 314, which expands into a discontinuity 216 in the wall of the hole 110 in strata 102 to transmit the force exerted by the force exerting apparatus 300 to which locking dog 314 is engaged to the strata 102 in which hole 110 is located. As shown in FIG. 8, the locking dog 314 is provided with a slide band advance nut 319 which moves along the threads 234 of the locking dog 314 when rotated to engage the slide band 248 and force the slide band 248 downwardly along the axis of the locking dog 314. The slide bank 248 is beveled as at reference numeral 236 to separate the radially extensible member 232 from the locking dog 314 and expand it radially outwardly to engage a discontinuity in the wall of hole 110 in the strata 102. This positive engagement enables the locking dog 314 to transmit the reactive forces to the strata 102. The locking dog 314 is also provided with selectively positionable means 318 for engaging the apparatus for exerting force along the line of action for transmitting the reactive force developed by the force exerting apparatus to which locking dog 314 is engaged, specifically, the plate 306 of derrick 300. Selectively positionable means 318 in the preferred embodiment is a locking nut.

The mechanism for transmitting a force into load bearing strata 102 with locking dog 314 is that of introducing an interference to carry shear forces between the wall of the hole 110 and locking dog 314. Such interference can be obtained by expanding the radially extensible member 232, as described above, into groove 216 or other types of discontinuity which causes "lock up" to be achieved. The discontinuity may be pre-existing, having been formed in the creation of the wall of the hole 110 of the strata 102, or the radially extensible means 232 may be used to create its own discontinuity in the wall of the hole 100. Those skilled in the art who have the benefit of this disclosure will recognize that further variations would likewise introduce such an interference between locking dog 314 and strata 102. For instance, as shown in FIG. 6A, radially projectible member 236, such as balls or pins, contained in retaining tracks 240 cut around the circumference of the locking dog 314' can be provided for this purpose. The tracks 240 are provided with lips (not numbered) to prevent the radially projecting member 236 from escaping from the track 20 while allowing partial protrusion through the track opening. Means 244 are driven vertically into drilled bores 246 in the locking dog 314', causing downward movement in the locking dog 314' of the end of the means 244 to cause the beveled surface 250 thereof to direct a horizontal component of force against the radially projecting member 236, causing the bearing 236 to engage the wall of hole 110 of the strata 102 with sufficient force to impress themselves into the wall of the hole 110 in the load bearing strata 102 sufficiently to create an interference fit for "lockup". The alternative embodiment of locking dog 314' shown in FIG. 6A has the advantage of not requiring the routing out of a discontinuity in the walls of the hole 110 in the case of certain strata. For instance, if strata 102 is concrete, the bearings 236 have sufficient "bite" to transfer the reactive forces to the concrete when forced outwardly into engagement with the concrete. By way of further example, epoxy or other substances that would harden in place can be injected in the retaining tracks 240 to thus achieve "lockup". An additional advantage of employing the locking dog 314 to achieve "lock up" is that it also enables locking dog 314 to carry torque.

Figure 10:
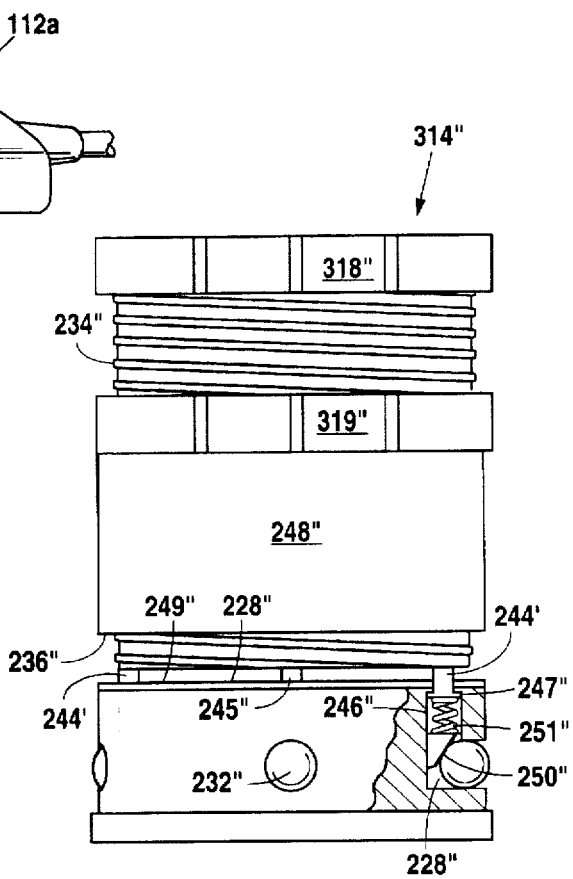
FIG. 10 is an elevational side view of a third alternative embodiment of the apparatus of FIG. 8.

A third embodiment of the means for positively engaging either the strata or the material through which a member is to be forced is shown in FIG. 10. In this third embodiment, indicated generally at reference numeral 314", there is provided a radially extensible member in the form of radially spaced ball bearings 232" resting in similarly spaced cavities 228" formed in the wall of locking dog 314". Locking dog 314" is also provided with a slide band advance nut 319" which moves along the threads 234" formed on the outside of locking dog 314" when rotated to engage and force the slide band 248" downwardly along the longitudinal axis of the right angle cylinder in which locking dog 314" is formed. Slide band 248" is provided with a bearing surface 236" for engaging the tops 245" of the pins 244" to cause the beveled surface 250 formed at the bottoms thereof to force the ball 232" radially outwardly to engage the wall (not shown) of the hole in which locking dog 314" is located. Each of the pins 244" is mounted in a bore 246" and retained therein by engagement of the shoulder 247" formed thereon with the keeper 249" which is secured to the shoulder 228" formed on the outside surface of locking dog 314". A spring 251" which is seated on the shoulder 253" formed in bore 246" and bears against the underside of the shoulder 247" of pin 244" biases the pin 244" upwardly to allow the radially extensible ball 232" to retract into the bore 246".

In materials which are loosely packed such as soil, the necessary interference between locking dog 314 and the material can be obtained from an auger or screw blade or screw threads (not shown) formed on the outside surface of the locking dog 314, and no groove or discontinuity 216 need be prepared. Such a locking dog is screwed into the material by equipping derrick 300 with a motor such as the motor described below for rotating a string of force transmitting members to drill through hard formations by mounting such a reactive force transmitting member on the end of the string by means of an adapter such as the adapter ring 384 described below. The ability of such a locking dog to resist movement along the longitudinal axis of the hole therethrough is directly dependent on the surface area of the blade of the screw threads or auger. Such structure can even be used successfully to transmit reactive forces to such loosely packed materials as sandy soil or loam by using a longitudinally extended reactive force transmitting apparatus with radially extending wings projecting therefrom that is impacted or forced into the material through which the member is to be forced. Other means for resisting such movement include the use of guy wires and soil anchors of various types known in the art and, as shown in FIG. 12, the plate 306 of derrick 300 is optionally provided with a plurality of holes 313 for receiving bolts (not shown) to attach force transmitting means 300 to an anchoring system engaging the load bearing strata 102. Alternatively, a separate means for anchoring force transmitting means 300 could be provided in the form of an L-bracket (or bracket shaped in any other appropriate configuration, also not shown) for transmitting the reactive force to, for instance, an adjacent concrete retaining wall, building structure, or even a piece of heavy equipment positioned for that purpose (not shown), thus eliminating the need for locking dog 314.

When a derrick 300 is equipped with a motor for rotating a string of force transmitting members such as the push rods 346 or 350 having a bit mounted thereto to drill through hard formations as described below, locking dog 314 must not only transmit the reactive forces of hydraulic cylinder 326 to strata 102 but must also resist or transfer counter-rotational force. Such resistance is achieved by the friction and interference created by circumferential contact of the radially extensible member 232 with the discontinuity in the wall of hole 110 of strata 102 or by one or more pointed projections or keys (not shown) extending radially outwardly from the outside surface of locking dog 314.

Referring now to FIGS. 11–14, there is shown a presently preferred embodiment of an apparatus for selecting the line of action along which a member is to be forced through soil or other materials. That line of action selecting means is, for convenience, referred to as a derrick and is indicated generally at reference numeral 300. Derrick 300 comprises a plurality of legs 302, having cams 303 pivotally mounted thereto for a purpose which will be made clear below, and upper 304 and lower 306 plate slidably mounted to the legs 302. Although the terms "upper" and "lower" have been used with regard to the description of the plate 304 and 306, it will be understood by those skilled in the art who have the benefit of this disclosure that derrick 300 need not be used in a position or orientation such that plates 304 and 306 are always "upper" and "lower". Derrick 300 can be used in any orientation, for instance on a slanted surface, vertical surface, or even "upside down". Consequently, the plates 304 and 306 may best be referred to as first and second plates, respectively, or even generically as plates 304 and 306.

For the same reason that plates 304 and 306 are not referred to as being "upper" and "lower" plates, derrick 300 is referred to as a means for selecting a line of action along which a member is to be forced. In other words, when positioned on a concrete slab, activation of hydraulic cylinder 326 results in a line of action which is exerted at substantially a right angle to that concrete slab. There is no requirement that the line of action be exerted at a right angle, however. Derrick 300 can be positioned on a platform (not shown) with an inclined surface or two of the legs 302 can simply be shorter than the other legs 302 such that the line of action is slanted with respect to the horizontal. Hence, the present specification refers to the line of action being exerted at an angle with respect to the strata or material through which a member is to be forced, it being recognized that the angle could be a ninety degree angle, or, for instance, a seventy degree angle such as might be used to place a soil anchor for a guy wire.

Means is provided for releasably securing plates 304 and 306 at a selected location along the legs 302 of derrick 300 in the form of the holes 308 spaced along the length of legs 302, the pins 310 slidably received within holes 308, and the holes (not numbered) in the blocks 312 which are attached to or integral with plates 304 and 306. The holes 312 could also be located in plates 304 and 306 such that blocks 312 are unnecessary. In a presently preferred embodiment, the legs 302 are provided with notches (not shown) along the length thereof instead of the holes 308 and, instead of the pins 310, the plates 304 and 306 are provided with rotating members extending therethrough having eccentric portions (not shown) mounted thereon for rotating into engagement with the notches. The ends of the rotating members are provided with handles to facilitate rotation thereof so that, once the plates 304 and/or 306 are positioned at the selected location along the legs, the members are rotated so as to cause their eccentric portions to rotate into engagement with the notch at that location. In a particularly preferred embodiment, the handles take the form of relatively heavy balls or other convenient shape mounted eccentrically on one or both ends of the rotating members with the eccentric portions of the rotating members being positioned relative to the eccentric balls so that when the action of gravity on the heavy balls causes the member to rotate, the eccentric portions are rotated into engagement with the notches in the legs 302.

Means is mounted to derrick 300 for transmitting reactive forces resulting from the resistance of the material, such as soil 204, to the forcing of a member therethrough in the form of locking dog 314 mounted in a hole (not numbered) in plate 306. As shown in more detail in FIGS. 12 and 14B, locking dog 314 is a tubular member as described above through which the member passes when the member forcing means, e.g., hydraulic cylinder 326, is activated and is provided with means for engaging derrick 300 in the form of nut 318 which is carried on the threads 320 cut into locking dog 314. Rotation of nut 318 relative to locking dog 314 causes axial movement of locking dog 314 relative to nut 318 because nut 318 rests on plate 306. A similar nut 319 is also carried on threads 320, but is positioned on the other side of plate 306 for advancing the slide band 248 downwardly along locking dog 314 to expand radially extensible member 232 radially outwardly into engagement with groove 214. In the preferred embodiment shown in FIGS. 11–14, plate 306 is provided with a "U"-shaped opening 311 on one side through which locking dog 314 is received by wheeling derrick 300 into engagement with the locking dog 314 after locking dog 314 has been placed in the hole 110. Before tightening the nut 318, a closure plate 315 (see FIG. 13) is dropped into the opening 311 to close that side of plate 306. The ears 317 of closure plate 315 rest on the shoulders 313 formed in the edges of plate 306 in the "U"-shaped opening 311.

Locking dog 314 and nut 318 are provided with a plurality of slots 322 for receiving a locking pin 324 for preventing rotational movement of nut 318 with respect to locking dog 314, thereby maintaining the snug engagement of strata 102 by locking dog 314. Additionally, insertion of locking pin 324 into one of the slots 322 allows the locking dog 314 and nut 318 to be rotated together on plate 306 without changing that snug engagement.

Referring to FIGS. 11 and 14A, means for forcing a member or device through the material such as soil 204 is mounted on the plate 304 in the form of a double acting hydraulic cylinder 326. It will be understood by those skilled in the art who have the benefit of this disclosure that hydraulic cylinder 326 is but one means of providing the force necessary to move such a member through such materials and that other means could also provide necessary force. Hydraulic cylinder 326 includes a ram 328 (see FIG. 14A) which passes through a hole 330 in first plate 304 and which is provided with means for releasably mounting a member or device thereto in the form of an end piece 332 mounted on the end thereof, for instance, on threads 333.

End piece 332 is provided with a slot 334 in one end thereof for receiving a locking pin 336 therethrough and multiple shoulders 338 and tapered planes 342 for engaging, aligning and seating a member or device, such as a force transmitting member or sample tube 340 when forced into the material such as soil 204, the nose 343 of end piece 332 being received within the interior diameter of the end of such members. The force transmitting members may take the form of push rods, two different embodiments of which are shown at reference numerals 346 (FIGS. 14 and 18) and 350 (FIGS. 11 and 15), both of which are included in the more generic term "member" which can be mounted to end piece 332. As end piece 332 is advanced against, for instance, push rod 350 (see FIG. 11), the upper margin of push rod 350 rides upon the tapered portion 342 of end piece 332, the incline of taper 342 causing lateral displacement of push rod 350 until the axis of push rod 350 is aligned with the axis of end piece 332. Alignment is further ensured by, and end piece 332 is capable of being used with members of different diameters because of, the plurality of tapers 342 and 342' and shoulders 338 and 338'.

As shown in FIG. 14A, end piece 332 is provided with an elongate slot 334 for receiving locking pin 336 therethrough to connect a force transmitting or other member thereto. Because the diameter of the nose 343 of end piece 332 is less than the internal diameter of the members such as push rods 346 or 350, or sample tube 340, the member can move and swing laterally from side-to-side as well as pivot on the axis of locking pin 336. The amount of lateral movement is controlled by the difference in the diameters of nose 343 and end piece 332, the extent to which the nose 343 extends into the member pinned thereto, and the internal diameter of the member pinned thereto. Lateral, swinging movement of the member pinned to end piece 332 greatly facilitates installation or removal of the member as well as other operations in which the member blocks access to the hole 110.

The force transmitting member can take several forms, one of which is a telescoping push rod 346 (FIGS. 14 and 18) made of several sections, three such sections being shown at reference numbers 349', 349" and 349'", each section 349 being provided with openings 348 spaced along the length thereof. A pin 347 is provided for placement in a selected opening of section 349' which is aligned with the openings 348 of the next smaller sections 349" and 349'" to hold the telescopic push rod 346 in the fully or partially extended or non-telescoped position. The telescoping ability of push rod 346 provides the ability to advance and/or retract a member mounted on the end thereof in a manner not limited by the length of the stroke of hydraulic cylinder 326. Likewise, the selective positioning of plate 304 to which the hydraulic cylinder 326 is mounted allows push rod 346 of a given length to be advanced or retracted by greater lengths than could be achieved if plate 304 were fixed along derrick legs 302.

Figure 18:
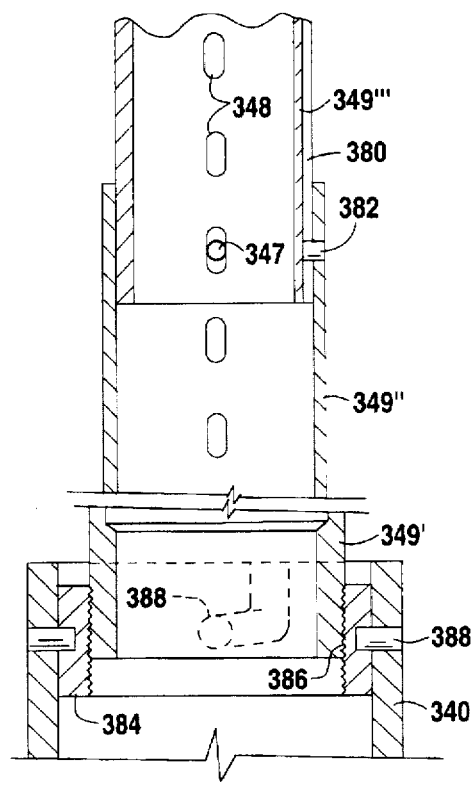
FIG. 18 is a longitudinal sectional, partially exploded view of a telescoping push rod for use with the apparatus of FIG. 11, having an adapter ring mounted thereto for engaging a member or device.

As shown in FIG. 18, each of the sections 349', 349", and 349'" of push rod 346 is provided with a longitudinal slot 380 having a pin or key 382 from the next larger telescoping section 349" or 349'" positioned therein to prevent rotational movement of each section 349 relative to the other sections 349. In that manner, the openings 348 in each section are kept in radial alignment, thereby facilitating insertion of the locking pin 347 in the desired opening 348 along the length of push rod 346. The openings 348 are vertically elongated to obviate the necessity for exact coincidence of the openings 348 of each section 349', 349" and 349'" before lock pin 347 can be inserted therethrough. In a preferred embodiment of the telescoping push rod 346 the outer surfaces of the smaller telescoping sections 349" and 349'" are modified along the vertically aligned openings 348 to provide clearance for any plastic deformation which may result at the lips of openings 348 due to repeated loadings upon the openings 348 at the locking pin 347. This clearance facilitating modification may be, but is not limited to, a "shaving" of the surfaces along the entire length of telescoping sections 349" and 349'" to create a "flat" (not shown) along the vertically aligned openings 348.

Section 349' (or push rod 350, not shown in FIGS. 14 and 18) is provided with an adapter ring 384 which is threadably received on the threads 386, or otherwise mounted, on section 349'. Adapter ring 384 is provided with radially extending pins 388 for engaging the J-slots 364 of a cylindrical member such as sample tube 340 as will be described. Adapter ring 384 also provides a convenient means for attaching other members (not shown), including, but not limited to, well casings, well points, benchmarks, soil anchors, penetrometers, piezometer tubes, soil gas samplers, stepped blade soil pressure transducers, or geophysical logging equipment, to push rods 346 or 350, and can be supplied in different sizes or having stepped threads for mounting members having different diameters to push rods 346 or 350. Such members can, of course, be mounted directly to the end of a push rod 346 or 350 as well.

An alternative embodiment of a force transmitting member for use in connection with the apparatus of the present invention and having a bayonet-type locking capability is shown at reference numeral 350 in FIGS. 11 and 15. Push rod 350 is mounted to end piece 332 using the same locking pin 336 and the openings 358 therein as used for push rod 346. The push rod 350 is provided at one end with four "J"-slots 352 having a slight taper in the bottom portion of the "J", as shown in FIG. 15. The other end of push rod 350 is provided with a portion 354 of slightly reduced diameter, the outside surface of the portion 354 being provided with four radially extending pins 356. The end of the push rod 350 having the "J"-slots 352 located therein is mated to the reduced diameter portion 354 of an adjoining push rod 350, the pins 356 are aligned with the "J"-slots 352, and the adjacent push rod (not shown) turned to snug the two push rods 350 to each other as a result of the taper in the "J"-slots 352. The taper in "J"-slots 352 insures that when the reduced diameter portion 354 of push rod 350 is advanced into larger diameter end 376 of an adjacent push rod 350, the shoulder 378 positively and securely engages the end 376 of the adjacent push rod 350 until rotational movement is used to unlock adjacent members. Engagement of the adjacent push rod 350 in this fashion increases the ability of each push rod 350 to efficiently transfer the force exerted by hydraulic cylinder 326 to the adjacent push rod 350, prevents excessive loading of pins 356, and securely connects and aligns the push rods 350 to each other.

As noted above, each push rod 346 or 350, as well as sample tube 340, is provided with the openings 348, 358 and 341, respectively, through which a pin (not shown) such as the pins 310 or the anti-drop washer 370 described below can be inserted to prevent push rods 346 or 350 or sample tube 340 from falling into the void created in the material under hole 110 or to provide a convenient point at which those members can be rotated to lock or unlock them from each other. The elongate member or anti-drop washer 370 prevents downward movement of those members by bearing against the top margin of locking dog 314 when sample tube 340 or push rods 346 or 350 extend downwardly therethrough. Alternatively, an arm (not shown) is mounted on a screw-in pivot pin on plate 306 which slides upon a shoe around the pivot pin and is provided with a projection, similar to the tang 374 (see below) of anti-drop washer 370, for engaging the holes 358 (or 348) in the push rod 346 or 350 to prevent downward movement of those members. To counteract the tendency for rotational movement of such an arm around the pivot pin caused by the weight of the members, the pin is provided with a ball, hook, or other structure over which a loop in the arm fits.

Figure 16:
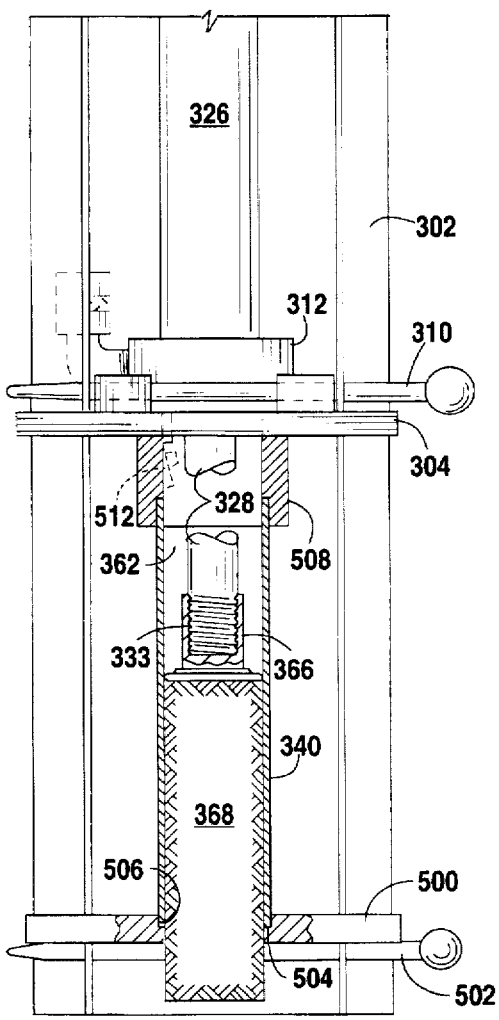
FIG. 16 is a sectional view of a portion of the apparatus of FIG. 11 in use for extruding a sample from a sample tube mounted thereto.

As shown in FIGS. 14A and 16, the derrick 300 is provided with means for preventing movement of the sample tube 340 relative to derrick 300 for the purpose of extruding the sample plug 368 therefrom. In the preferred embodiment shown in FIG. 14, this movement preventing means takes the form of an extruder plate 500 which is mounted to derrick 300 on the pins 502 which are removably inserted through the holes (not numbered) in the legs 302 of derrick 300 having a hole 504 therethrough and means formed in the wall of the hole 504 for engaging the sample tube 340 to prevent movement thereof when the hydraulic cylinder 326 is activated to advance the plunger 366 mounted on the threads 333 of the ram 328 thereof down through the sample tube 340. In the embodiment shown in FIG. 16, this sample tube engaging means takes the form of a shoulder 506 formed in the wall of the hole 504 through plate 500 on which sample tube 340 rests.

Also provided is means for aligning the longitudinal axis of sample tube 340 with the ram 328 of hydraulic cylinder 326 for guiding the plunger 366 mounted thereto into the sample tube 340 to extrude the sample plug 368 therefrom. In the preferred embodiment, the aligning means is a tube guide 508 screwed into the plate 304 of derrick 300 on the threads 510 formed in the walls of a hole (not numbered) in plate 304 for that purpose and having an internal diameter selected so as to closely approximate the diameter of the outside surface of the sample tube 340 from which the plug 368 is to be extruded. Alternatively, the tube guide 508 is mounted on the ram 328 of hydraulic cylinder 326 concentrically with plunger 366. Either way, once the sample tube 340 is placed on the shoulder 506 formed in the hole through extruder plate 500 (the center of the hole being aligned with the ram 328) and the other end of the sample tube 340 is aligned with the axis of the ram 328, by tube guide 508, plunger 366 is advanced into sample tube 340 without hanging up on the top edges thereof or binding on the inside of the tube 340. Although not necessary to the function of the tube guide 508, and therefore shown in shadow lines in FIG. 16, the inside walls of the tube guide 508 can be tapered, as at reference numeral 512, for further centering of the plunger 366 at entry into the bottom opening of the tube guide 508 for engaging the top edge of the tube 340.

The means for preventing movement, and providing alignment, of sample tube 340 relative to derrick 300 and plunger 366 is shown in an alternative embodiment in FIG. 14A. As shown in that figure, the hole 330 in upper plate 304 is threaded for receiving the threaded end of extruder head 360. Extruder head 360 is provided with means for releasably mounting a member such as a sample tube 340 to prevent movement of the member when hydraulic cylinder 326 is activated in the form of four pins 362 extending inwardly for receiving the "J"-slots 364 in the top of sample tube 340 (FIG. 14B). Sample tube 340 is secured to extruder head 360 by removing any push rods 346 or 350 which may be pinned to end piece 332, aligning pins 362 with "J"-slots 364, inserting the top of the sample tube 340 into extruder head 360, and rotating sample tube 340 with respect to extruder head 360, the taper in the bottom of the "J"-slots 364 causing sample tube 340 to move upwardly to seat against the shoulder 361 of extruder head 360. When plunger 366 is screwed onto the threads 333 on the end of the ram 328 of hydraulic cylinder 326 (shown in FIG. 16) and hydraulic cylinder 326 is activated, the sample plug 328 is extruded from sample tube 340. Those skilled in the art can see that the "J"-shots in the sample tubes 340 can also greatly facilitate quick attachment and detachment from or mounting on the end of push rod 350.

Although hydraulic cylinder 326 is capable of considerable force when activated to force a member through a material such as the soil 204 even when the material is hard, i.e., high clay content, rock, etc., there are certain formations that cannot be breached without drilling. The structure of derrick 300 is adaptable for drilling through such formations. The ram 238 of hydraulic cylinder 326 turns freely within hydraulic cylinder 326 such that all that is necessary to impart rotational motion to a string of force transmitting members such as push rods 346 or 350 is a motor, which can be hydraulic powered by the same hydraulic fluid which powers hydraulic cylinder 326, and teeth or other means for translating the rotational motion of such a motor to the string such as is well known in the art. Likewise, a suitable thrust bearing, mounted between end piece 332 and the force transmitting members, allows rotation of the force transmitting members while at the same time transmitting the thrust forces developed by hydraulic cylinder 326 thus obviating rotation of the hydraulic ram components. The member mounted on the end of the string is, of course, a drill bit of the appropriate size, mounted by an adapter ring such as adapter ring 384 having a coupling mechanism resistant to rotational movement in the direction of rotation of the bit as is also well known in the art.

As has been described, it is often advantageous to disconnect sample tube 340, push rods 346 and 350, or any other member mounted to end piece 332, from end piece 332 while preventing vertical movement with respect to the other components of derrick 300 such as locking dog 314. Disconnecting those members is especially advantageous in operations such as those which are described below that a core from which the sample tube 340 or push rod 346 or 350 is extracted during operations. In such an operation, for instance a material sampling operation, progressive shortening of the string of push rods 346 or 350 to retrieve the soil sample necessitates that the push rods 346 or 350 be released or disengaged with respect to each other or released or disengaged from end piece 332 from time to time. Disconnecting those cylindrical members creates the possibility that the string can fall "down the hole". To prevent loss of the string down-hole, either the above-described pivot arm is used or an elongate member similar to the pin 502 is inserted through one of openings 348 or 358 through the wall of one of the push rods 346 or 350, the ends of pin 502 resting on the top of locking dog 314, thereby preventing downward movement of the entire string.

Figure 17:
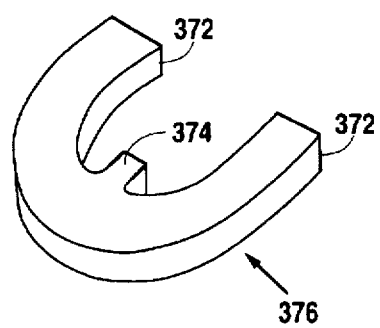
FIG. 17 is a perspective view of an anti-drop washer for use in practicing the method of the present invention.

Referring to FIG. 17, there is shown another means of preventing such downward movement relative to locking dog 314 in the form of the above-described anti-drop washer 370, the inside surface of which is shaped to approximate the surface contour of a member which is cylindrical, i.e., sample tube 340 or push rods 346 or 350. The two ears 372 of washer 370 fit fairly closely around the outer surface of such cylindrical members. At a location along the inside surface of ears 372, a tang 374 is provided for projecting into any one of the holes 341 in sample tube 340, or the holes 348 or 358 in push rod 346 or 356 when the ends 372 of anti-drop washer 370 encircle the sample tube 340, or the push rod 346 or 356. When, for instance, sample tube 340 is in the position shown in FIG. 12, the tang 374 of anti-drop washer 370 (not shown in FIG. 12) is inserted into hole 341 and anti-drop washer 370 rests on top of locking dog 314 to prevent vertical movement of sample tube 340 with respect to locking dog 314.

As will be apparent from the foregoing description, a member mounted on end piece 332 can be forced deeper into a material such as the soil 204 by extending the string of force transmitting members to which the member, such as sample tube 340, is mounted. However, those skilled in the art will recognize that, as the string is extended, the weight of the string increases, increasing the difficulty of handling the string. Consequently, one of the uses of a pin such as the pin 502 and holes 341, 348, and 358 is for handling the string. For instance, when pin 502 extends through holes 348 in the uppermost push rod 346 or 350 and the uppermost push rod 346 or 350 is detached from end piece 332, the entire string can be rotated manually by grasping pin 502 and exerting force thereon to rotate the string until the "J"-slots 352 are aligned with the pins 356 on a push rod 346 or 350 which has just been mounted on end piece 332 or until the holes 348 therein are aligned with the slot 334 in end piece 332 for receiving lock pin 336, as the case may be. Further, rotation of the string is also used to advantage to place a well casing, well point, benchmark, soil anchor, or other member or device in the soil 204 or other material. Such members are mounted to an adapter ring 384 or to the end of the force transmitting member such that all that is required to disconnect such members from adapter ring 384 or the force transmitting member to leave such members in the material 204 is relative counter-rotational movement such as can be achieved using one of the pins 502 in this manner.

With reference to the preceding detailed description of the presently preferred embodiments of the invention, the method of the present invention will now be described with particular reference to obtaining a soil sample and extruding that sample on-site. As set out above, a hole 110 is first drilled through strata 102 and, referring to FIGS. 2 and 3, a discontinuity or groove 215 is routed out in the wall of the hole 110 in strata 102. Although strata 102 and soil 204 are shown in FIG. 14 as separate facies, i.e., a concrete slab poured over soil, it will be understood by those skilled in the art who have the benefit of this disclosure that the operation of the apparatus of the present invention and methods described herein do not require such sites. Strata 102 could be a natural formation of rock, a layer of asphalt, clay or caliche, or even tightly compacted soil such that the material which is to be sampled is itself the load bearing strata 102. Hence, there is no line of demarcation between facies shown in FIG. 5.

The point at which material is to be removed from the wall of hole 110 to form discontinuity or groove 216 is selected by loosening the jam nut 138 on the housing 106 of groover tool 100, rotating the locating lug 132 to the desired location on the threads of housing 106, and then snugging jam nut 138 up against lug nut 132 to prevent subsequent rotational movement of locating lug 132 relative to housing 106. The depth of the groove 216 in the wall of hole 202 is then selected by press fitting a depth control ring 140 of the appropriate thickness around the outer circumference of locating lug 132.

Locking dog 314 is positively engaged to the material through which the member is to be forced by placing into hole 110 and advancing the slide band 248 downwardly along locking dog 314 by rotating the nut 319 on threads 320 on the outside surface of locking dog 314. The radially extensible member 232 is urged outwardly into the groove 216 by the bevel in slide band 248 shown in FIG. 14B. Positive engagement of strata 102 (or any material) in that fashion prevents axial movement of locking dog 314 in hole 110 regardless of the direction of the reactive forces applied thereto.

The locking dog 314 in hole 110 is then engaged by rolling derrick 300 over the hole 110 and turning the nut 318 carried on threads 320 until snugged tightly against plate 306. Nut 318 and locking dog 314 are releasably locked using the locking pin 324. If it is desired to snug derrick 300 up to strata 102 to reduce "play" in the system, locking dog 314 is grasped to prevent rotation, locking pin 321 is removed, and nut 318 is rotated to move locking dog 314 upwardly to progressively increase the load bearing against lower plate 306.

Referring to FIG. 11, to position upper plate 304, which carries force exerting means 326, pins 310 are removed and plate 304 is moved vertically by manually sliding plate 304 to the desired location along derrick legs 302 and then locked at that height by locking pins 310 through openings 308 of derrick legs 302 and blocks 312. Plate 304 is preferably provided with handles 307 to facilitate manual positioning thereof.

Alternatively, plate 304 is raised or lowered to the desired position by releasing locking pins 310 from blocks 312 and holes 308 in legs 302 of derrick 300 and activating hydraulic cylinder 326 to extend ram 328 until end piece 332 bears against the top of a plate (not shown) or other suitable flat surface placed over the top of locking dog 314. Once end piece 332 encounters the plate, or is otherwise stopped from further downward movement as described below, the pins 310 in the blocks 312 of upper plate 304 are removed from legs 302 so that further extension of ram 328 raises upper plate 304 and hydraulic cylinder 326. Once upper plate 304 has reached the desired position, locking pins 310 are re-inserted through openings 308 in legs 302 and blocks 312, thus achieving selective positioning of upper plate 304 on derrick 300. Ram 328 need not bear against a plate resting on top of locking dog 314. All that is necessary is that ram 328 encounter resistance against continued extension. Resistance could be supplied by a block of wood, a push rod 346 or 350, a pin 310 placed in slot 334 in end piece 332, or even a pin or other convenient component placed in one of the holes 308 to prevent downward movement of ram 328.

As an alternative to the use of locking pins 310 to position plate 304, the legs 302 are provided with notches (not shown) along the length thereof instead of the holes 308 and, instead of the pins 310, the plates 304 and 306 are provided with rotating members extending therethrough having eccentric portions (not shown) mounted thereon for rotating into engagement with the notches. The ends of the rotating members are provided with handles in the form of relatively heavy balls or other convenient shape mounted eccentrically on one or both ends of the rotating members with the eccentric portions of the rotating members being positioned relative to the eccentric bails so that when the action of gravity on the heavy balls causes the member to rotate, the eccentric portions are rotated into engagement with the notches in the legs 302. Plate 304 may then be raised either manually or by extending the ram 328, as described above, simply by lifting the handles on the ends of the rotating members until the eccentric portions disengage with the notches in legs 302, this enables "hands free" operation with respect to plate 304, if using ram 328, because the plate is free to travel along the legs 302 upon clearing the notch. Upon contact with the next notch on legs 302, gravity acts upon the heavy end of the plate's rotating member to cause the member's eccentric portions to engage that notch. In this manner, plate 304 may travel up the length of legs 302 by disengaging the eccentric portion of the plate's rotating members at each notch until the desired height is reached.

Referring to FIG. 14A, once hydraulic cylinder 326 is positioned at the desired height, a force transmitting member such as push rod 346 or 350 is mounted on end piece 332. Mounting is accomplished by retracting ram 328 and lifting push rod 346 or 350 vertically into the space between end piece 332 and the top of locking dog 314. A pin 310 is inserted through the openings 348 and the lower end of push rod 346 or 350 is grasped in one hand while the top of push rod 346 or 350 is grasped with the other. Push rod 346 or 350 is then manually lifted and positioned so that the nose 343 of end piece 332 extends into the hollow end of the push rod 346 or 350. The openings 348 at the top of push rod 346 or 350 are then aligned with the slot 334 on end piece 332 and pin 336 is inserted. In the case of push rod 346, which is of the telescoping variety, the components 349', 349", and 349"', etc. are restrained from telescoping movement by pin 347 extending through any suitable opening 348 therethrough.

Sample tube 340 or other member is attached to the lower end of push rod 346 or 350 directly or by means of the adapter ring 384 as shown in FIG. 18. The "J"-slots 364 of sample tube 340 are aligned with the pins 383 of adapter ring 384 and hydraulic cylinder 326 is then activated, and by extension of ram 328, sample tube 340 and push rod 346 or 350 are moved through the bore of locking dog 314 until contact with material such as the soil 204 is made. At this point, the top margin of push rod 346 or 350 and the shoulder 338 of end piece 332 are aligned and seated as previously described. Further downward extension of ram 328 causes downward movement of push rods 346 or 350 and sample tube 340 into soil 204 along the line of action selected with derrick 300. That downward movement creates a reactive force equal and in the opposite direction to the driving force which tends to push derrick 300 in a direction opposite that line of action, i.e., at an angle away from the load bearing strata 102. Movement of derrick 300 is restrained, however, by engagement of derrick 300, particularly locking dog 314, with load bearing strata 102. The reactive forces resulting from the resistance of the soil to the forcing of the member through the material are thus transmitted from sample tube 340 to the hydraulic cylinder 326, to upper plate 304 across pins 310, into legs 302 of derrick 300, across pins 310 to lower plate 306, and into locking dog 314 by bearing of lower plate 306 against nut 318, and through radially extensible member 232 into the discontinuity or groove 216 in load bearing strata 102. As noted above, those reactive forces can be transmitted to any material and/or load hearing strata, or the material and strata can be one and the same.

As discussed previously, discontinuity 216 can be located at any point in the hole 110 in strata 102. In certain instances, it is desirable to locate discontinuity 216 at or near the bottom of hole 110. In such instances, there is no bottom surface of the discontinuity 216, or the strata 102 may be of insufficient thickness to develop the required strength, and downward forces on collar 200 cannot be effectively resisted in the manner described above. However, by action of axles 322 and wheels 320 or by pivoting of cams 303 into contact with strata 102, reactive forces can be effectively transmitted to the load bearing strata 102. In some applications, the reactive forces can be better transmitted to strata 102 by mounting a cylinder (not shown) having a radially extending plate at the bottom end thereof to the threads 320 in locking dog 314 in place of nut 319. The plate transmits force to strata 102 around the same radius as the force transmitted through radially extensible member 232 and discontinuity 216, and the cylinder can be screwed downwardly into engagement with strata 102 to effectively place the portion of strata 102 between radially extensible member 232 and the plate in compression rather than tension. Such structure is particularly useful in applications in which the material comprising strata 102 is not compacted as, for instance, when strata 102 is itself the material through which the member is to be forced, e.g., the soil to be sampled.

Upon maximum extension of ram 328, further advancement of sample tube 340 is accomplished by extending the string of push rods 346 or 350. If a push rod of the type shown at reference numeral 346 is being used, ram 328 is retracted slightly, thus loosening the shear force on and allowing the removal of pin 347, and the portions 349', 349" and 349'", etc. are telescoped with respect to one another by further retraction of ram 328, causing section 349'" to be extended from the nested portion within the other sections 349' and 349". The holes 348 in respective sections 349', 349" and 349'" are longitudinally aligned and pin 347 is reinserted, thus locking telescoping sections 349', 349" and 349'" together and resulting in extension of the length of the push rod 346. Hydraulic cylinder 326 is then activated, further advancing sample tube 340 until additional extension is required. Retraction of the push rod 346 is performed in a similar manner, and a pin or anti-drop washer 370 is used for both extension and retraction to facilitate the handling of the string of members.

If a push rod of the type shown at reference numeral 350 is being used, ram 328 is also backed off slightly, a pin 310, the pivot arm described above, or anti-drop washer 370 is inserted into one of the openings 358, and the pin 336 is then retracted from slot 334 and uppermost push rod 350. Ram 328 is then fully retracted, an additional push rod 350 is pinned to end piece 332, and ram 328 is extended until the pins 356 of the additional push rod 350 engage the "J"-slots 352 of the formerly uppermost push rod 350 resting on the top of locking dog 314. The string of push rods 350 extending down through hole 110 is then rotated with respect to the newly added push rod 350 to lock onto that newly-added push rod 350.

Sample tube 340 is advanced until the material or soil 204 fills the bore thereof or the desired sampling depth is reached, after which sample tube 340 is retracted. During retraction, the direction of the reactive forces is the reverse of the direction of those forces resulting from forcing the member into the soil 204, and referring to FIG. 14B, the reactive forces are transmitted through the legs 302 of derrick 300 and are transferred across axles 322 and through wheels 320 to the load bearing strata 102. As noted above, the legs 302 of derrick 300 are provided with cams 303, pivotally mounted to legs 302, which are pivoted into contact with load bearing strata 102 to function as load bearing members rather than wheels 320 and axles 322. Alternatively, the reactive forces resulting from retraction are transferred into the locking dog 314 in positive engagement with strata 102 by the nut 319 that is threaded onto locking dog 314 under and in contact with plate 306. A pin similar to pin 310 is inserted in an opening 308 just above lower plate 306 so that downward forces in the legs 302 of derrick 300 are transferred across pin 310 into lower plate 306 onto lower nut 319, into locking dog 314, and into load bearing strata 102 by means of radially extensible member 232 and discontinuity 216 when the cylindrical member is retracted.

Preferably, ram 328 is retracted only to a point at which a portion of the member such as sample tube 340, or a section 349', 349", or 349'" of push rod 346, or push rod 350, projects above the top of locking dog 314. Once that point is reached, the member is counter-rotated to disengage that member from the pins 356 (or 388 in the case of an adapter ring 384 mounted thereto). Rotation is facilitated by insertion of pins similar to that shown at reference numeral 310 into the hole 341 of sample tube 340 or holes 348 of push rod 346 or 350, as the case may be. Pins 310 are used as a "cheater bar" for rotating the members for disengagement from each other and to prevent the member from falling back into the hole 110 once disengaged from adapter ring 384 or adjacent member. Once disconnected, push rod 346 or 350 is conveniently moved laterally by swinging on pin 336 or by movement of pin 336 in slot 334, so that the cylindrical member can be withdrawn without obstruction.

After removal of sample tube 340, another sample tube 340 is placed in the bore of locking dog 314 using a pin 310, pivot arm, or anti-drop washer 370 to prevent falling into that bore. Push rod 346 or 350 is swung into alignment with sample tube 340 and the adapter ring 384 is engaged thereto. The anti-drop washer 370, pivot arm, or pin 310 then is removed and hydraulic cylinder 326 activated to move sample tube 340 into contact with material 204 where sampling operations are resumed.

After the required number of material samples are obtained and sample tube 340 has been disengaged from adapter 352, the samples are removed from the bore of sample tube 340 as follows. The push rods 346 or 350 are released from end piece 332 and end piece 332 unscrewed from the end of ram 328. Plunger 366 (see FIG. 16) is then screwed onto the threads 333 on the end of ram 328 and the ram 328 is retracted all the way up into extruder head 360. A sample tube 340 containing a sample 368 therein is mounted to extruder head 360 by alignment of pins 362 with "J"-slots 364 and then applying counter-rotation. Hydraulic cylinder 326 is then activated to advance plunger 366 against the material sample 368 contained within sample tube 340, thus extruding sample 368. Plunger 366 is then retracted, the now-empty sample tube 340 is removed from extruder head 360 and another sample tube 340 containing another sample is mounted thereto for repetition of that same process.

Although the invention has been described in terms of the above-characterized presently preferred embodiments, it will be understood by those skilled in the art who have the benefit of this disclosure that changes can be made to these embodiments without departing from the spirit and scope of the invention. It is envisioned that such changes would be included within the following claims.

What is claimed is:

1. An apparatus for removing material from a hole in a strata comprising:

a) a drive shaft rotatably mounted within a housing and having a cutting blade mounted on one end thereof for removing material from a hole in a strata, the other end of said drive shaft being adapted for engaging power means for rotating said drive shaft;

b) a locating means mounted on the outside surface of said housing and having means extending therefrom for supporting said housing over the hole with the cutting blade extending into the hole to a location which can be changed by movement of said locating means relative to said housing; and c) means for selectively preventing movement of said locating means relative to said housing to maintain the cutting blade at a location in the hole.

2. The apparatus of claim 1 additionally comprising means releasably mounted to said housing for changing the depth to which material removal is to be performed at the selected location in the hole.

3. The apparatus of claim 2 wherein said depth changing means comprises a depth control ring of selected thickness applied to the outer surface of said locating means.

4. The apparatus of claim 2 wherein said depth changing means comprises a semicircular member applied to the surface of said locating means.

5. The apparatus of claim 1 wherein said locating means comprises a lug having threads formed thereon for riding on threads formed on the outside surface of said housing and a plurality of radially extending spokes for resting on the surface of the strata when the cutting blade extends into the hole in the strata.

6. The apparatus of claim 5 wherein said movement preventing means comprises a threaded jam nut riding on the threads formed on said housing.

7. The apparatus of claim 5 wherein said movement preventing means comprises a set screw extending from said lug into a slot formed in said housing.

8. The apparatus of claim 5 wherein said lug is provided with a shroud.

9. The apparatus of claim 2 wherein said shroud is provided with a lip extending over the ends of the spokes of said lug.

10. The apparatus of claim 1 additionally comprising a shroud slip fit over said housing for containing the material in the hole during removal with the cutting blade.

11. The apparatus of claim 10 wherein said shroud is provided with a nozzle.

12. A method of forcing a member into a material comprising the steps of:
 a) drilling a hole in a material;
 b) creating a discontinuity in the hole;
 c) engaging the discontinuity with a tubular member having a bore therethrough;
 d) forcing a member into the hole through the bore in the tubular member and into the material; and
 e) transmitting the reactive forces resulting from the resistance of the material to the forcing of the member into the discontinuity in the material through the tubular member.

13. The method of claim 12 additionally comprising positively engaging the material into which the member is forced.

14. The method of claim 12 additionally comprising positively engaging a strata overlying the material into which the member is forced.

15. The method of claim 12 wherein the discontinuity is engaged by expanding means located on the outside surface of the tubular member into the discontinuity.

16. The method of claim 12 wherein the discontinuity is created by removing material from a surface from within the hole.

17. The method of claim 16 additionally comprising controlling the amount of material removed from the surface of the material.

18. An apparatus for removing material from a hole in a strata comprising:
 an elongate, rotatable member having means mounted on one end thereof for removing material comprising a strata from the wall of a hole in the strata, the other end of said rotatable member being adapted for engaging means for rotating said rotatable member;
 means mounted to said rotatable member comprising a generally round housing having threads formed on the outside surface thereof and a threaded lug which is moved relative to said rotatable member on the threads for supporting said rotatable member over the hole in the strata with the material removing means extending into the hole to a location selected by moving said supporting means relative to said rotatable member; and
 means for preventing movement of said supporting means relative to said rotatable member to maintain the material removing means at the selected location in the hole.

19. The apparatus of claim 18 wherein said supporting means additionally comprises means extending radially outwardly from said threaded lug.

20. The apparatus of claim 18 wherein said movement preventing means comprises a threaded jam nut.

21. The apparatus of claim 18 wherein said lug is provided with a plurality of outwardly extending spokes.

22. The apparatus of claim 21 wherein said movement preventing means comprises a set screw in said lug and a slot formed in said housing for receiving said set screw therein.

23. The apparatus of claim 18 wherein said support means comprises means extending outwardly from said rotatable member for supporting the material removing means in the hole so that material is removed in a plane substantially parallel to the surface of the strata.

24. An apparatus for removing material from a hole in a strata comprising:
 an elongate, rotatable member having means mounted on one end thereof for removing material comprising a strata from the wall of a hole in the strata, the other end of said rotatable member being adapted for engaging means for rotating said rotatable member;
 a support comprised of a housing having said rotatable member journaled therein and a lug carried on the outside surface of said housing and selectively positionable thereon for supporting said rotatable member over the hole in the strata with the material removing means extending into the hole to a location selected by moving said lug relative to said housing; and
 means for preventing movement of said lug relative to said housing to maintain the material removing means at the selected location in the hole.

25. The apparatus of claim 24 wherein said lug is provided with threads for riding on threads formed on said housing.

26. The apparatus of claim 25 wherein said movement preventing means comprises a threaded jam nut.

27. The apparatus of claim 24 wherein said lug is provided with a plurality of spokes extending outwardly therefrom for resting on the surface of the strata when said rotatable member is positioned in the hole in the strata.

28. The apparatus of claim 24 wherein said movement preventing means comprises a set screw for engaging said housing.

29. The apparatus of claim 28 wherein said housing is provided with a plurality of detents for receiving said set screw therein.

30. The apparatus of claim 28 wherein said housing is provided with a slot for receiving said set screw therein.

31. A method of removing a material comprising a strata from a surface from within a hole in the strata comprising the steps of:
 supporting a material removing means on the surface of the strata at a selected location in a hole in a strata;
 sliding the material removing means on the surface of the strata to engage the selected location within the hole from which material is to be removed; and
 preventing movement of the material removing means which would change the selected location at which material is removed.

32. The method of claim 31 additionally comprising covering the hole in the strata to contain the material being removed from within the hole in the strata.

33. The method of claim 31 additionally comprising controlling the amount of material removed from within the hole in the strata.

34. The method of claim 31 additionally comprising stabilizing the material removing means as material is removed from within the hole in the strata.

35. The method of claim 31 additionally comprising mounting depth control means to the material removing means whereby the depth of the material removed from within the hole in the strata is controlled by contact of the depth control means with the wall of the hole when the material removing means slides on the surface of the strata.

* * * * *